US009737523B2

(12) United States Patent
Ghahary et al.

(10) Patent No.: US 9,737,523 B2
(45) Date of Patent: Aug. 22, 2017

(54) ANTI-FIBROGENIC COMPOUNDS, METHODS AND USES THEREOF

(71) Applicant: The University of British Columbia, Vancouver (CA)

(72) Inventors: Aziz Ghahary, Vancouver (CA); Yunyuan Li, Vancouver (CA); Ruhangiz T. Kilani, Vancouver (CA); Ryan Hartwell, Vancouver (CA)

(73) Assignee: THE UNIVERSITY OF BRITISH COLUMBIA, Vancouver (CA)

( * ) Notice: Subject to any disclaimer, the term of this patent is extended or adjusted under 35 U.S.C. 154(b) by 0 days.

(21) Appl. No.: 14/896,269

(22) PCT Filed: Jun. 4, 2014

(86) PCT No.: PCT/CA2014/000484
§ 371 (c)(1),
(2) Date: Dec. 4, 2015

(87) PCT Pub. No.: WO2014/194407
PCT Pub. Date: Dec. 11, 2014

(65) Prior Publication Data
US 2016/0120857 A1 May 5, 2016

Related U.S. Application Data

(60) Provisional application No. 61/831,404, filed on Jun. 5, 2013.

(51) Int. Cl.
*A61K 31/47* (2006.01)
*A61K 31/198* (2006.01)

(52) U.S. Cl.
CPC ............ *A61K 31/47* (2013.01); *A61K 31/198* (2013.01)

(58) Field of Classification Search
CPC .............................. A61K 31/47; A61K 31/198
USPC ......................................................... 514/311
See application file for complete search history.

(56) References Cited

U.S. PATENT DOCUMENTS

2008/0161353 A1  7/2008  Barnham et al.

FOREIGN PATENT DOCUMENTS

| EP | 1369114 A1 | 12/2003 |
|---|---|---|
| WO | WO 2004/007461 A1 | 1/2004 |
| WO | WO 2008/087461 | 7/2008 |
| WO | WO 2013/186355 | 12/2013 |

OTHER PUBLICATIONS

Chen et al International Journal of tryptophan Research, 2009, 2, 1-19.*

Poormasjedi-Meibod, M-S. et al., "Anti-Scarring Properties of Different Tryptophan Derivatives," PLOS One, pp. e91955 (1-13), vol. 9, No. 3.
Chavez-Munoz, C. et al., "Application of an Indoleamine 2,3-Dioxygenase-Expressing Skin Substitute Improves Scar Formation in a Fibrotic Animal Model." *Journal of Investigative Dermatology*, Feb. 2012, 132(5):1501-1505, doi: 10.1038/jid.2011.467.
Forouzandeh, F. et al., "Local expression of indoleamine 2,3-dioxygenase suppresses T-cell-mediated rejection of an engineered bilayer skin substitute." *Wound Repair and Regeneration*, 2010, 18(6):614-623, doi: 10.1111/j.1524-475X.2010.00635.x.
Iannitti, R.G. et al., "Th17/Treg Imbalance in Murine Cystic Fibrosis Is Linked to Indoleamine 2,3-Dioxygenase Deficiency but Corrected by Kynurenines." *American Journal of Respiratory and Critical Care Medicine*, Mar. 2013, 187(6):609-620, doi: 10.1164/rccm.201207-1346OC.
Li, Y. et al., "Kynurenine Increases Matrix Metalloproteinase-1 and -3 Expression in Cultured Dermal Fibroblasts and Improves Scar (Continued)

*Primary Examiner* — Yevegeny Valenrod
(74) *Attorney, Agent, or Firm* — Saliwanchik, Lloyd & Eisenschenk

(57) ABSTRACT

Presented herein are methods for treatment of diseases or conditions related to fibrosis. Compounds, or pharmaceutically acceptable salts thereof or pharmaceutical compositions thereof provide for the treatment of diseases or conditions related to fibrosis. The methods utilize the compounds kynurenine, kynurenic acid and xanthurenic acid, and various analogs, related structures and pharmaceutical compositions thereof, wherein the compounds are represented by one or more compounds represented by Formulas I, II, or II as set out below:

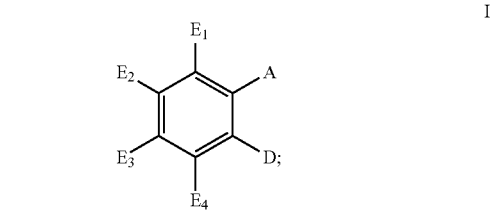

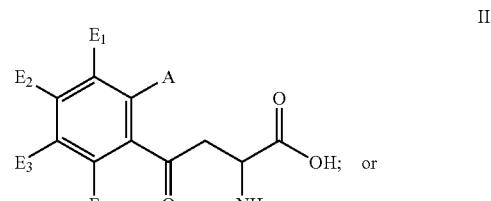

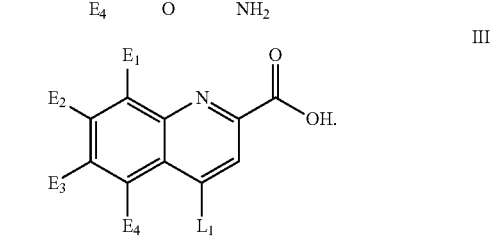

17 Claims, 18 Drawing Sheets

(56) References Cited

OTHER PUBLICATIONS ring In Vivo." *Journal of Investigative Dermatology*, Oct. 2013, 134(3):643-650, doi: 10.1038/jid.2013.303.

* cited by examiner

A

B

C

A

Synoviocytes

B

IMR-90

A

Kynurenine (100 μg/ml)  − − − − + + + +

PD98059 (μM)  0  1  10  30  0  1  10  30

MMP-1

β-actin

B

PD98059 (30 μM)      +                  +

U0126 (30 μM)           +                  +

U0126 (10 μM)                  +                  +

Kynurenine  − − − − + + + +

MMP-1

β-actin

A

B

C

D

ANTI-FIBROGENIC COMPOUNDS, METHODS AND USES THEREOF

CROSS REFERENCE TO RELATED APPLICATIONS

This application is the U.S. national stage application of International Patent Application No. PCT/CA2014/000484, filed Jun. 4, 2014, which claims priority from U.S. Provisional Application Ser. No. 61/831,404, entitled "ANTI-FIBROGENIC COMPOUNDS AND METHODS" filed Jun. 5, 2013.

FIELD OF THE INVENTION

The present invention relates to novel methods for the treatment of fibrosis. More specifically, the description provided herein relates to the use of kynurenine, kynurenic acid, xanthurenic acid, and/or related compounds for the treatment of fibrotic disease, in particular diseases or conditions of the skin such as keloids and hypertrophic scarring.

BACKGROUND OF THE INVENTION

Fibrosis, a disorder belonging to a group of fibroproliferative conditions, is seen in different organs such skin, liver, lung, kidney and arteries. It is estimated that approximately 40% of all deaths in the United States are caused, in part, by fibroproliferative disorders. Excessive accumulation of extracellular matrix due to either over production of matrix such as fibronectin, type I and III collagens, low levels of matrix degrading enzymes such as matrix metalloproteinases (MMPs) or both are the common features of all of these fibrotic conditions.

As in all other organs, wound healing in the skin is a dynamic process involving tissue response to different types of insults. This process involves a continuous sequence of signals and responses in which platelets, fibroblasts, epithelial, endothelial and immune cells come together outside of their usual domain in order to orchestrate the very complex process of tissue repair. These signals, which are mainly growth factors (GFs) and cytokines, orchestrate the initiation, continuation and termination of wound healing (Scott et al. 1994). An imbalance in the synthesis and release of cytokines and GFs at the wound site may result in either retarded wound healing (e.g. in diabetic and elderly populations) or over-healing (e.g. fibroproliferative disorders, complication following surgical incision, traumatic wounds, and severe thermal injury). Thus, an important component of wound healing is its timely cessation and without such a timely cessation there may be a buildup of excess matrix, a deleterious fibrotic condition seen in millions of patients worldwide.

Matrix metalloproteinases (MMPs) represent a group of diverse proteolytic enzymes involved in ECM turnover and connective tissue remodeling during physiological conditions such as embryonic growth and development, uterine involution, bone growth, bone resorption and wound healing. The level of MMP expression in normal cells is low and that allows healthy connective tissue remodeling. However, an imbalance in expression of MMPs has been implicated in a number of pathological conditions such as dermal fibrosis, rheumatoid arthritis, atherosclerosis, and tumor invasion and metastasis.

Current treatment modalities for any fibrotic condition including dermal fibro-proliferating disorders such as hypertrophic scarring (HSc) and keloid remain unsatisfactory. Accordingly, it would be desirable to have therapeutic strategies for the treatment of various fibrotic diseases and conditions.

SUMMARY

The present invention is based, in part, on the surprising discovery that certain compounds—kynurenine and its analogues/isoforms, kynurenic acid, and xanthurenic acid—are capable of stimulating MMP1 and MMP3 expression, while inhibiting collagen and fibronectin expression. Furthermore, as described herein these compounds, when applied in vivo, are capable of inhibiting, preventing or reducing the formation of keloid scar.

In one embodiment, there is provided a use of a compound, the compound having the structure of Formula I:

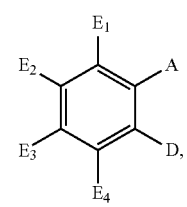

wherein, $E_1$ may be H, OH, $NH_2$, R, OR, NHR, $NR_2$, SH, SR, F, Cl, Br, or I; $E_2$ may be H, OH, $NH_2$, R, O, NHR, $NR_2$, SH, SR, F, Cl, Br, or I; $E_3$ may be H, OH, $NH_2$, R, OR, NHR, $NR_2$, SH, SR, F, Cl, Br, or I; $E_4$ may be H, OH, $NH_2$, R, OR, NHR, $NR_2$, SH, SR, F, Cl, Br, or I; R may be a 1 to 20 carbon group that may be optionally saturated, unsaturated, linear, branched linear, cyclic, branched cyclic, aromatic, partially aromatic or non aromatic, where each carbon may be optionally replaced by O, S, SO, $SO_2$, NH, or NR', and each carbon may be optionally substituted with one or more of: OH, OR', R', F, Cl, Br, I, =O, SH, SR', $NH_2$, NHR', $N(R')_2$, $OSO_3H$, $OPO_3H_3$, $CO_2H$, $CON(R')_2$ and $CO_2R'$; R' may be independently selected from the group consisting of: a one to ten carbon group that is optionally saturated, unsaturated, linear, branched linear, cyclic, branched cyclic, aromatic, partially aromatic or non aromatic; A may be H, or $NH_2$; D may be

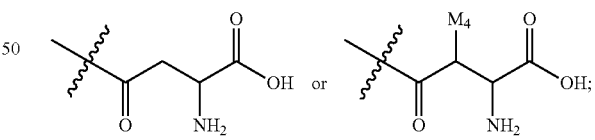

or A and D may form a six membered ring, selected from the following:

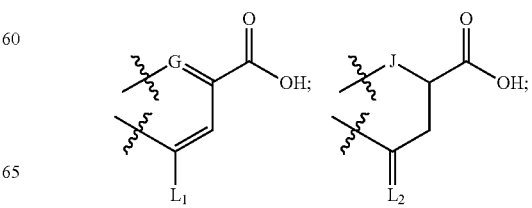

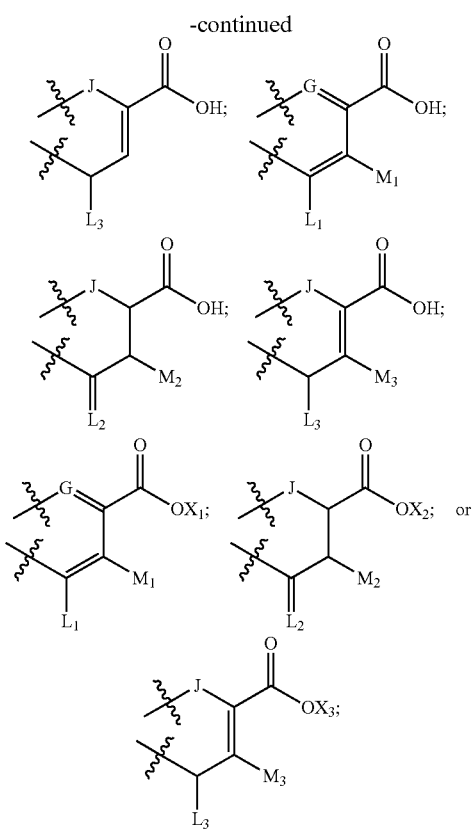

may be CH or N; J may be S or O; $L_1$ may be OH, OQ, $NH_2$, NHQ, $NQ_2$, SH, or SQ; $L_2$ may be O, SQ', or NQ'; $L_3$ may be OH, OQ, $NH_2$, NHQ, $NQ_2$, SH, or SQ; Q may be a 1 to 20 carbon group that may be optionally saturated, unsaturated, linear, branched linear, cyclic, branched cyclic, aromatic, partially aromatic or non aromatic, where each carbon may be optionally replaced by O, S, SO, $SO_2$, NH, or NQ', and each carbon may be optionally substituted with one or more of: OH, OQ', Q', F, Cl, Br, I, =O, SH, SQ', $NH_2$, NHQ', $N(Q')_2$, $OSO_3H$, $OPO_3H_3$, $CO_2H$, $CON(Q')_2$ and $CO_2Q'$; Q' may be independently selected from the group consisting of: a one to ten carbon group that is optionally saturated, unsaturated, linear, branched linear, cyclic, branched cyclic, aromatic, partially aromatic or non aromatic; $M_1$ may be H, OH, $NH_2$, T, OT, NHT, $NT_2$, SH, ST, F, Cl, Br, or I; $M_2$ may be H, OH, $NH_2$, T, OT, NHT, $NT_2$, SH, ST, F, Cl, Br, or I; $M_3$ may be H, OH, $NH_2$, T, OT, NHT, $NT_2$, SH, ST, F, Cl, Br, or I; $M_4$ may be OH, $NH_2$, T, OT, NHT, $NT_2$, SH, ST, F, Cl, Br, or I; T may be H, or a 1 to 20 carbon group that may be optionally saturated, unsaturated, linear, branched linear, cyclic, branched cyclic, aromatic, partially aromatic or non aromatic, where each carbon may be optionally replaced by O, S, SO, $SO_2$, NH, or NT', and each carbon may be optionally substituted with one or more of: OH, OT', T', F, Cl, Br, I, =O, SH, ST', $NH_2$, NHT', $N(T')_2$, $OSO_3H$, $OPO_3H_3$, $CO_2H$, $CON(T')_2$ and $CO_2T'$; T' may be independently selected from the group consisting of: a one to ten carbon group that may be optionally saturated, unsaturated, linear, branched linear, cyclic, branched cyclic, aromatic, partially aromatic or non aromatic; $X_1$ may be H, OH, $NH_2$, Z, OZ, NHZ, $NZ_2$, SH, SZ, F, Cl, Br, or I; $X_2$ may be H, OH, $NH_2$, Z, OZ, NHZ, $NZ_2$, SH, SZ, F, Cl, Br, or I; $X_3$ is H, OH, $NH_2$, Z, OZ, NHZ, $NZ_2$, SH, SZ, F, Cl, Br, or I; and Z may be a 1 to 20 carbon group that is optionally saturated, unsaturated, linear, branched linear, cyclic, branched cyclic, aromatic, partially aromatic or non aromatic, where each carbon may be optionally replaced by O, S, SO, $SO_2$, NH, or NZ', and each carbon may be optionally substituted with one or more of: OH, OZ', Z', F, Cl, Br, I, =O, SH, SZ', $NH_2$, NHZ', $N(Z')_2$, $OSO_3H$, $OPO_3H_3$, $CO_2H$, $CON(Z')_2$ and $CO_2Z'$; and Z' may be independently selected from the group consisting of: a one to ten carbon group that may be optionally saturated, unsaturated, linear, branched linear, cyclic, branched cyclic, aromatic, partially aromatic or non aromatic; for either the treatment of fibrotic disease or for the manufacture of a medicament to treat fibrotic disease.

In a further embodiment, there is provided a method of treating fibrotic disease, the method comprising administering to a mammalian cell a compound or pharmaceutically acceptable salt thereof, the compound having the structure of Formula I.

In a further embodiment, there is provided a method of treating fibrotic disease, the method comprising administering to a mammalian cell a compound or pharmaceutically acceptable salt thereof, the compound having the structure of Formula II.

In a further embodiment, there is provided a method of treating fibrotic disease, the method comprising administering to a mammalian cell a compound or pharmaceutically acceptable salt thereof, the compound having the structure of Formula III.

In a further embodiment, there is provided a method of treating fibrotic disease, the method comprising administering to a subject in need thereof, a compound or pharmaceutically acceptable salt thereof, the compound having the structure of Formula I.

In a further embodiment, there is provided a method of treating fibrotic disease, the method comprising administering to a subject in need thereof, a compound or pharmaceutically acceptable salt thereof, the compound having the structure of Formula II.

In a further embodiment, there is provided a method of treating fibrotic disease, the method comprising administering to a subject in need thereof, a compound or pharmaceutically acceptable salt thereof, the compound having the structure of Formula III.

In a further embodiment, there is provided a pharmaceutical composition for treating fibrotic disease, the pharmaceutical composition comprising a compound or pharmaceutically acceptable salt thereof and a pharmaceutically acceptable excipient, wherein the compound has the structure of Formula I.

In a further embodiment, there is provided a pharmaceutical composition for treating fibrotic disease, the pharmaceutical composition comprising a compound or pharmaceutically acceptable salt thereof and a pharmaceutically acceptable excipient, wherein the compound has the structure of Formula II.

In a further embodiment, there is provided a pharmaceutical composition for treating fibrotic disease, the pharmaceutical composition comprising a compound or pharmaceutically acceptable salt thereof and a pharmaceutically acceptable excipient, wherein the compound has the structure of Formula III.

In a further embodiment, there is provided a pharmaceutical composition, the pharmaceutical composition comprising a compound or pharmaceutically acceptable salt thereof and a pharmaceutically acceptable excipient, wherein the compound has the structure of Formula I.

In a further embodiment, there is provided a pharmaceutical composition, the pharmaceutical composition comprising a compound or pharmaceutically acceptable salt thereof and a pharmaceutically acceptable excipient, wherein the compound has the structure of Formula II.

In a further embodiment, there is provided a pharmaceutical composition, the pharmaceutical composition comprising a compound or pharmaceutically acceptable salt thereof and a pharmaceutically acceptable excipient, wherein the compound has the structure of Formula III.

In a further embodiment, there is provided a commercial package comprising (a) a pharmaceutical composition described herein; and (b) instructions for the use thereof for treating fibrotic disease.

In a further embodiment, there is provided a commercial package comprising (a) a compound of Formula I; and (b) instructions for the use thereof for treating fibrotic disease.

In a further embodiment, there is provided a commercial package comprising (a) a compound of Formula II; and (b) instructions for the use thereof for treating fibrotic disease.

In a further embodiment, there is provided a commercial package comprising (a) a compound of Formula III; and (b) instructions for the use thereof for treating fibrotic disease.

In a further embodiment, there is provided a compound of Formula I for the treatment of fibrotic disease.

In a further embodiment, there is provided a compound of Formula II for the treatment of fibrotic disease.

In a further embodiment, there is provided a compound of Formula III for the treatment of fibrotic disease.

The fibrotic disease may be selected from one or more of the following: keloid; hypertrophic scaring; pulmonary fibrosis; kidney fibrosis; liver cirrhosis; chronic inflammation of tunica albugenia (CITA); endomyocardial fibrosis; mediastinal fibrosis; myelofibrosis; retroperitoneal fibrosis; progressive massive fibrosis; nephrogenic systemic fibrosis; Crohn's disease; old myocardial infarction; scleroderma; systemic sclerosis; uterine fibroids; and restenosis.

Q may be a 1 to 6 carbon group that is optionally saturated, unsaturated, linear, branched linear, cyclic, branched cyclic, aromatic, partially aromatic or non aromatic. R may be a 1 to 6 carbon group that is optionally saturated, unsaturated, linear, branched linear, cyclic, branched cyclic, aromatic, partially aromatic or non aromatic. T may be a 1 to 6 carbon group that is optionally saturated, unsaturated, linear, branched linear, cyclic, branched cyclic, aromatic, partially aromatic or non aromatic. Z may be a 1 to 6 carbon group that is optionally saturated, unsaturated, linear, branched linear, cyclic, branched cyclic, aromatic, partially aromatic or non aromatic.

Q' may be a 1 to 6 carbon group that is optionally saturated, unsaturated, linear, branched linear, cyclic, branched cyclic, aromatic, partially aromatic or non aromatic. R' may be a 1 to 6 carbon group that is optionally saturated, unsaturated, linear, branched linear, cyclic, branched cyclic, aromatic, partially aromatic or non aromatic. T' may be a 1 to 6 carbon group that is optionally saturated, unsaturated, linear, branched linear, cyclic, branched cyclic, aromatic, partially aromatic or non aromatic. Z' may be a 1 to 6 carbon group that is optionally saturated, unsaturated, linear, branched linear, cyclic, branched cyclic, aromatic, partially aromatic or non aromatic.

$E_1$ may be H, OH, $NH_2$, $OCH_3$, $CH_3$, SH, F, Cl, Br, or I. $E_2$ may be H, OH, $NH_2$, $OCH_3$, $CH_3$, SH, F, Cl, Br, or I. $E_3$ may be H, OH, $NH_2$, $OCH_3$, $CH_3$, SH, F, Cl, Br, or I. $E_4$ may be H, OH, $NH_2$, $OCH_3$, $CH_3$, SH, F, Cl, Br, or I. A may be H or $NH_2$. D may be

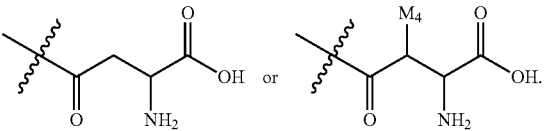

Alternatively, A and D may form a 6 membered ring selected from the following:

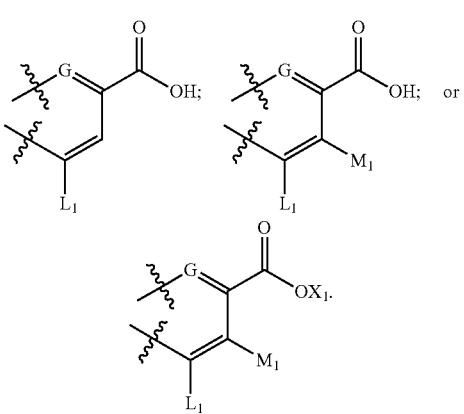

G may be CH or N. $L_1$ is OH, $NH_2$, or SH. $M_1$ may be H, OH, $NH_2$, SH, F, Cl, Br, or I. $M_4$ may be OH, $NH_2$, SH, F, Cl, Br, or I. $X_1$ may be H, OH, $NH_2$, SH, F, Cl, Br, or I.

$E_1$ may be H, OH, $NH_2$, $OCH_3$, or $CH_3$. $E_2$ may be H, OH, $NH_2$, $OCH_3$, or $CH_3$. $E_3$ may be H, OH, $NH_2$, $OCH_3$, or $CH_3$. $E_4$ may be H, OH, $NH_2$, $OCH_3$, or $CH_3$. A may be H or $NH_2$. D may be

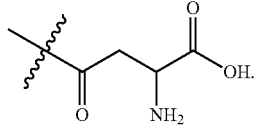

Alternatively, A and D may form a 6 membered ring selected from the following:

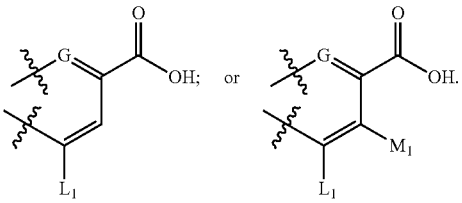

G may be CH or N. $L_1$ may be OH or $NH_2$. $M_1$ is H, OH, or $NH_2$.

$E_1$ may be H, OH, $NH_2$, $OCH_3$, or $CH_3$. $E_2$ may be H, OH, $NH_2$, $OCH_3$, or $CH_3$. $E_3$ may be H, OH, $NH_2$, $OCH_3$, or $CH_3$. $E_4$ may be H, OH, $NH_2$, $OCH_3$, or $CH_3$. A may be H, or $NH_2$. D may be

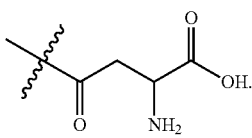

Alternatively, A and D may form a 6 membered ring having the following structure:

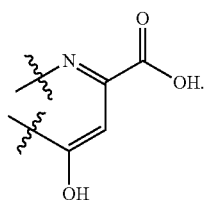 [SMILES: */N=C(\C=C(/*)O)C(=O)O]

$E_1$ may be H, OH, or $NH_2$. $E_2$ may be H, OH, or $NH_2$. $E_3$ may be H, OH, or $NH_2$. $E_4$ may be H, OH, or $NH_2$. A may be H, or $NH_2$. D may be

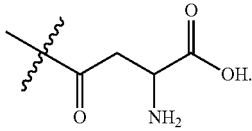 [SMILES: *C(=O)CC(N)C(=O)O]

Alternatively, A and D may form a 6 membered ring having the following structure:

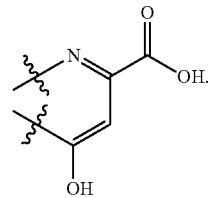 [SMILES: */N=C(\C=C(/*)O)C(=O)O]

The compound may have the structure of Formula II:

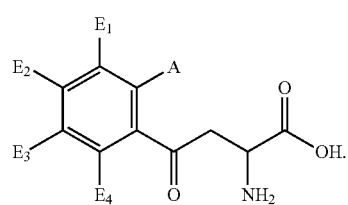

The compound may have the structure of Formula III:

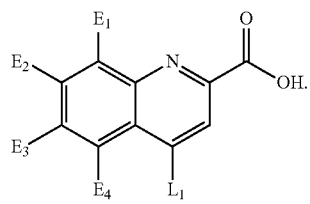

$L_1$ may be OH or $NH_2$. $L_1$ may be OH. $E_1$ may be H or OH. $E_2$ may be H, OH, or $NH_2$. $E_3$ may be H, OH, or $NH_2$. $E_4$ may be H, OH, or $NH_2$.

$E_1$ may be H, OH, or $NH_2$. $E_2$ may be H or OH. $E_3$ may be H, OH, or $NH_2$. $E_4$ may be H, OH, or NH.

$E_1$ may be H, OH, or $NH_2$. $E_2$ may be H, OH, or $NH_2$. $E_3$ may be H or OH. $E_4$ may be H, OH, or $NH_2$.

$E_1$ may be H, OH, or $NH_2$. $E_2$ may be H, OH, or $NH_2$. $E_3$ may be H or OH. $E_4$ may be H or $NH_2$.

$E_1$ may be H or OH. $E_2$ may be H or OH. $E_3$ may be H or OH. $E_4$ may be H or $NH_2$.

The compound may be selected from one or more of the following:

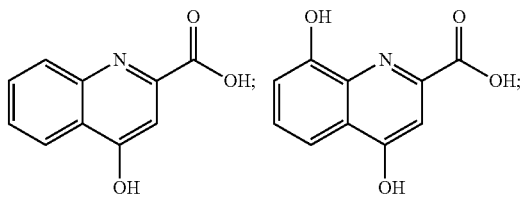

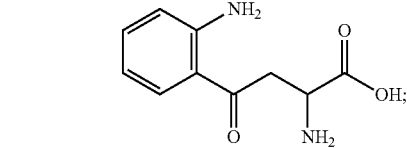

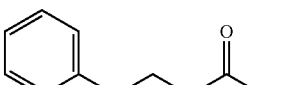

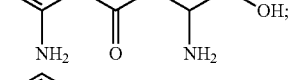

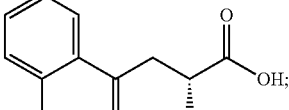

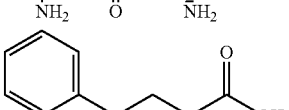

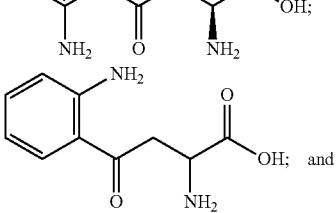

-continued

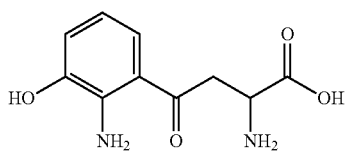

The compound may be selected from one or more of the following:

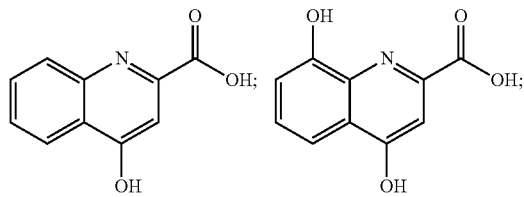

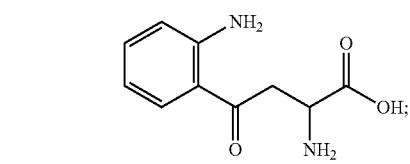

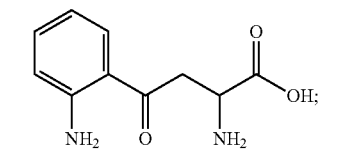

The compound may be

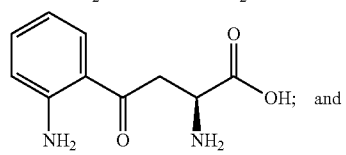

The compound may be

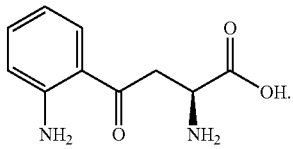 [SMILES: Nc1ccccc1C(=O)C[C@H](N)C(=O)O]

The compound may be

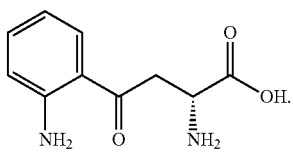

The compound may be

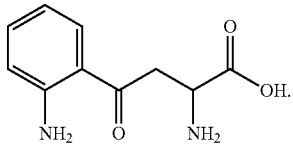 [SMILES: Nc1ccccc1C(=O)CC(N)C(=O)O]

The compound may be

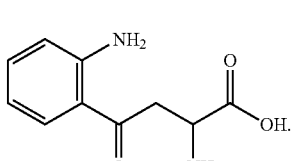

The compound may be

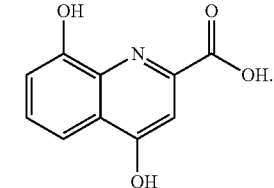 [SMILES: O=C(O)c1cc(O)c2cccc(O)c2n1]

The compound may be

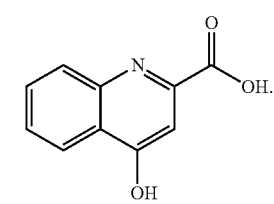 [SMILES: O=C(O)c1cc(O)c2ccccc2n1]

DETAILED DESCRIPTION

Figure 1:
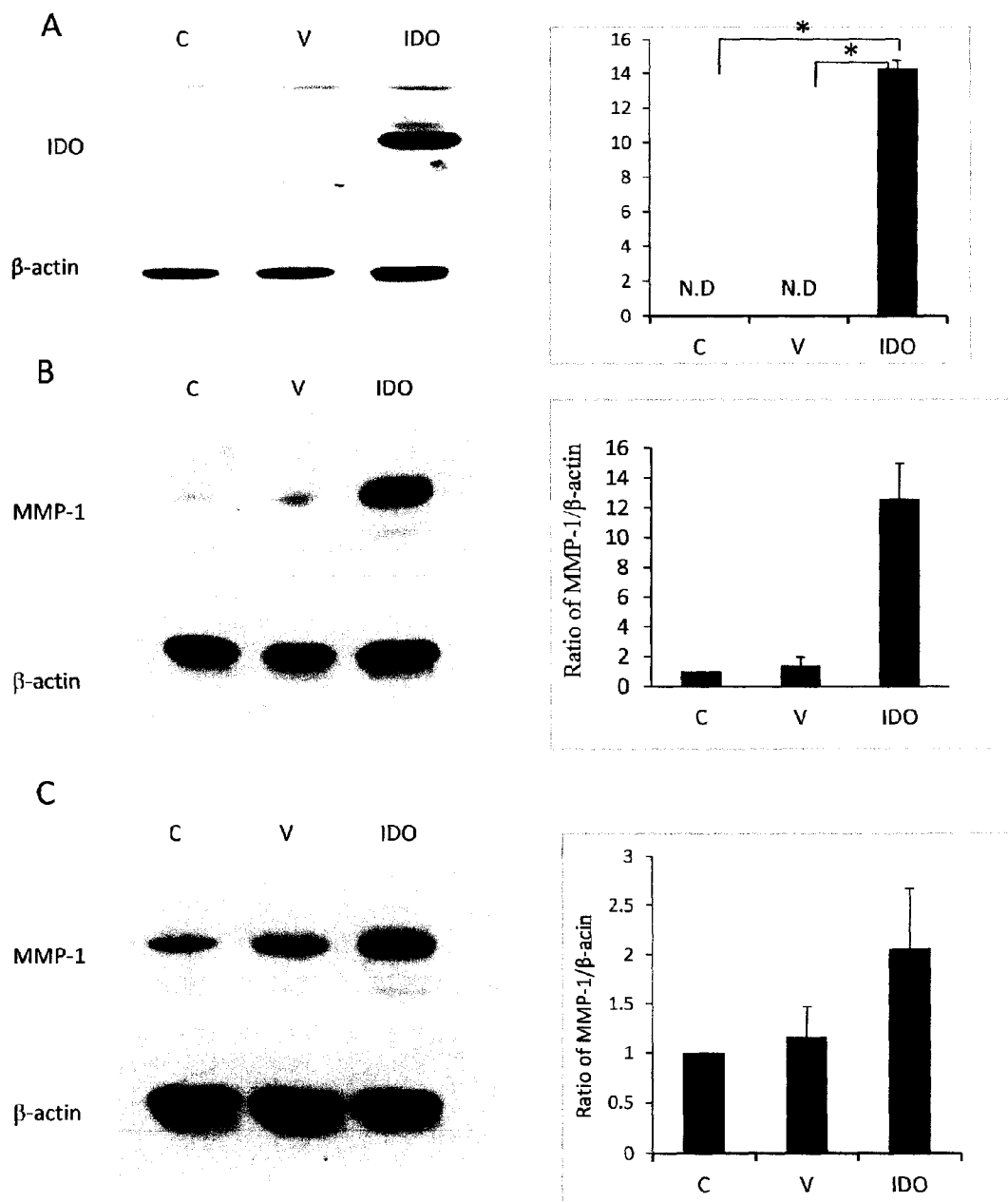
FIG. 1: Indoleamine 2,3-Dioxygenase (IDO) up-regulation of MMP-1 expression in human dermal fibroblasts. Panel A shows fibroblasts that were transduced with either nothing (C), adenoviral vector (V) or a vector bearing the IDO recombinant gene (IDO) for 48 hrs, where IDO and its activity was detected by Western blotting (left Panel) and measurement of the kynurenine levels (right panel), respectively (N.D indicates the level of kynurenine was not detectable). Panel B shows both untreated, adenoviral vector, and IDO-transduced fibroblasts, that were lysed after being cultured for 48 hours, and the expression of MMP-1 was detected by Western blotting. Panel C shows fibroblasts that were incubated with the conditioned media taken from either control, empty vector or IDO adenoviral vector-transduced fibroblasts for 48 hours, where the expression of MMP-1 was analyzed by Western blotting. β-actin was used as a loading control in panels A, B and C. * indicates p<0.001.

Any terms not directly defined herein shall be understood to have the meanings commonly associated with them as understood within the art of the invention. As employed throughout the specification, the following terms, unless otherwise indicated, shall be understood to have the following meanings.

As used herein a 'subject' refers to an animal, such as a bird or a mammal. Specific animals include rat, mouse, dog, cat, cow, sheep, horse, pig or primate. A subject may further be a human, alternatively referred to as a patient. A subject may further be a transgenic animal. A subject may further be a rodent, such as a beaver, mouse or a rat.

As used herein, an 'inhibitor' refers to a drug, compound or an agent that restrains or retards a physiological, chemical or enzymatic action or function. An inhibitor may cause at least 5% decrease in enzyme activity. An inhibitor may also refer to a drug, compound or agent that prevents or reduces the expression, transcription or translation of a gene or protein.

'Indoleamine 2,3-Dioxygenase', or 'IDO', is a heme-containing rate limiting enzyme that catalyzes tryptophan to N-formylkynurenine and then to kynurenine (Kyn), and is found in non-hepatic cells mainly in macrophages and trophoblasts. Recent findings have implicated catabolism of tryptophan, an essential amino acid, by IDO as being involved in immune tolerance (Kahari and Saarialho-Kere 1997). As demonstrated herein, kynurenine, as well as its breakdown products kynurenic acid and xanthurenic acid, induce MMP-1 and MMP-3, as well as showing a reduction of fibrosis in vitro and in vivo.

The 'matrix metalloprotease', or 'MMP' family consist of 25 zinc- and calcium-dependent proteinases in the mammalian system. According to their substrate specificity, primary structure and cellular localization, 5 different subfamilies of closely related members known as collagenases, gelatinases, stromelysins, matrilysins, and membrane-type MMPs have been identified (Murphy et al. 2002). From all of these MMPs, MMP1 is the major enzyme involved in the collagenolytic process, breaking down the interstitial collagens such as types I, II, and III, while MMP-3 (stromelysin-1) is a protease known to degrade mainly the noncollagenous portion of the ECM such as fibronectin, proteoglycans, and laminin (Kahari and Saarialho-Kere 1997). Increases in both MMP1 and MMP-3 expressions and released by fibroblasts can initiate degradation of almost all major components of the ECM (Saus et al. 1988). It is now accepted that MMPs produced by keratinocytes facilitate epithelial migration, while MMPs expressed by fibroblasts promote tissue remodeling (Salo et al. 1991).

'Fibrosis' is a general terms that involves the formation or development of excess fibrous connective tissue in an organ or tissue as a reparative or reactive process, as opposed to a formation of fibrous tissue as a normal constituent of an organ or tissue. Scarring is confluent fibrosis that obliterates the architecture of the underlying organ or tissue. There are many diseases and/or conditions that are characterized by or associated with fibrosis, including, but not limited to: keloid, hypertrophic scar, pulmonary fibrosis, kidney fibrosis, liver cirrhosis, chronic inflammation of tunica albugenia (CITA), endomyocardial fibrosis, mediastinal fibrosis, myelofibrosis, retroperitoneal fibrosis, progressive massive fibrosis, nephrogenic systemic fibrosis, Crohn's disease, old myocardial infarction, scleroderma, and systemic sclerosis.

There are provided herein a number of compounds for use in the treatment of diseases or conditions characterized by or related to fibrosis. In the context of the current description, the term 'treatment' may refer to treatment of existing fibrosis or fibrotic disease, or alternately may refer to treatment which occurs before or during the fibrotic process in order to prevent the development or progression of fibrosis. The compounds described herein may be in isolation, or may be linked to or in combination with tracer compounds, liposomes, carbohydrate carriers, polymeric carriers or other agents or excipients as will be apparent to one of skill in the art. In an alternate embodiment, such compounds may comprise a medicament, wherein such compounds may be present in a pharmacologically effective amount. The compounds may be suitable for administration to a subject in need thereof, by virtue of the fact that the subject may benefit from prophylaxis or treatment of fibrosis or fibrotic disease. The compounds may also include tautomers or stereoisomers.

As used herein "FS" refers to FibroStops (for example, FS1 is used as an abbreviation for kynurenine (or DL-kynurenine or DL-Kyn) and FS2 or KA may be used as an abbreviation for kynurenic acid). L-kynurenine may be represented herein as L-Kyn and D-kynurenine may be represented herein as D-Kyn. Similarly, xanthurenic acid may be represented herein as XA.

The term 'medicament' as used herein refers to a composition that may be administered to a patient or test subject and is capable of producing an effect in the patient or test subject. The effect may be chemical, biological or physical, and the patient or test subject may be human, or a non-human animal, such as a rodent or transgenic mouse, or a dog, cat, cow, sheep, horse, hamster, guinea pig, rabbit or pig. The medicament may be comprised of the effective chemical entity alone or in combination with a pharmaceutically acceptable excipient.

The term 'pharmaceutically acceptable excipient' may include any and all solvents, dispersion media, coatings, antibacterial, antimicrobial or antifungal agents, isotonic and absorption delaying agents, and the like that are physiologically compatible. An excipient may be suitable for intravenous, intraperitoneal, intramuscular, subcutaneous, intrathecal, topical or oral administration. An excipient may include sterile aqueous solutions or dispersions for extemporaneous preparation of sterile injectable solutions or dispersion. Use of such media for preparation of medicaments is known in the art.

Compositions or compounds according to some embodiments may be administered in any of a variety of known routes. Examples of methods that may be suitable for the administration of a compound include orally, intravenous, inhalation, intramuscular, subcutaneous, topical, intraperitoneal, intra-rectal or intra-vaginal suppository, sublingual, and the like. The compounds described herein may be administered as a sterile aqueous solution, or may be administered in a fat-soluble excipient, or in another solution, suspension, patch, tablet or paste format as is appropriate. A composition comprising the compounds described herein may be formulated for administration by inhalation. For instance, a compound may be combined with an excipient to allow dispersion in an aerosol. Examples of inhalation formulations will be known to those skilled in the art. Other agents may be included in combination with the compounds described herein to aid uptake or metabolism, or delay dispersion within the host, such as in a controlled-release formulation. Examples of controlled release formulations will be known to those of skill in the art, and may include microencapsulation, embolism within a carbohydrate or polymer matrix, and the like. Other methods known in the art for making formulations are found in, for example, "Remington's Pharmaceutical Sciences", (19th edition), ed. A. Gennaro, 1995, Mack Publishing Company, Easton, Pa.

The dosage of the compositions or compounds of some embodiments described herein may vary depending on the route of administration (oral, intravenous, inhalation, or the like) and the form in which the composition or compound is administered (solution, controlled release or the like). Determination of appropriate dosages is within the ability of one of skill in the art. As used herein, an 'effective amount', a 'therapeutically effective amount', or a 'pharmacologically effective amount' of a medicament refers to an amount of a medicament present in such a concentration to result in a therapeutic level of drug delivered over the term that the drug is used. This may be dependent on mode of delivery, time period of the dosage, age, weight, general health, sex and diet of the subject receiving the medicament. Methods of determining effective amounts are known in the art.

In one embodiment, there is provided a method for treatment of a subject having or suspected of having a fibrotic disease, the method comprising administering to the subject a therapeutically effective amount of a compound having a structure corresponding to Formula I, II, or III. The fibrotic disease may be one of the following: keloid, hypertrophic scar, pulmonary fibrosis, kidney fibrosis, liver cirrhosis, chronic inflammation of tunica albugenia (CITA), endomyocardial fibrosis, mediastinal fibrosis, myelofibrosis, retroperitoneal fibrosis, progressive massive fibrosis, nephrogenic systemic fibrosis, Crohn's disease, old myocardial infarction, scleroderma, systemic sclerosis, uterine fibroids, restenosis.

Materials and Methods

Cell Cultures

Neonatal foreskin and joints used as the sources of fibroblasts, keratinocytes and synoviocytes. The procedures were done based on the approval of Human Ethics Committee of the University of British Columbia. Cultures of human foreskin fibroblasts were established as described previously (Li et al., 2006). Briefly, foreskin was collected and washed three times with Dulbecco's Modified Eagle Medium (DMEM; GIBCO™, Grand Island, N.Y.) supplemented with antibiotic-antimycotic preparation (100 u/ml penicillin, 100 µg/ml streptomycin, 0.25 µg/ml amphotericin B) (Invitrogen Life Technologies™, Gaithersburg, Md.). Specimens were dissected free of fat and minced into small pieces less than 2.0 mm in diameter, washed six times with DMEM, distributed into 60×15-mm Petri dishes and incubated at 37° C. in a water-jacked humidified incubator in an atmosphere of 5% $CO_2$. The medium was replaced twice weekly. Upon reaching confluence, the cells were released by trypsinization (0.1% trypsin, Invitrogen Life Technologies™) and (0.02% EDTA, Sigma™, St. Louis, Mo.), split for subculture at a ratio of 1:6, and reseeded onto 75-cm² flasks. Fibroblasts from passages 3-7 were used for this study.

Human foreskin keratinocytes were established as previously described (Ghahary et al., 1998). Cells were cultured in serum-free keratinocyte medium (KSFM; Invitrogen Life Technologies™) supplemented with bovine pituitary extract (50 µg/ml) and EGF (0.2 ng/ml). These cells were used at passages 2-5.

Synoviocytes were obtained by enzymatic digestion of synovial membrane from patients with rheumatoid arthritis during joint replacement with 1 mg/ml collagenase (Sigma™) in RPMI1640 (Invitrogen Life Technologies™) for 4 hours at 37° C. Dissociated cells were plated in synoviocyte growth medium (Cell Applications Inc.™, San Diego, Calif.) supplemented with penicillin G sodium (100 U/mL), streptomycin sulfate (100 µg/mL), and amphotericin B (0.25 µg/mL). Synoviocytes were found to be morphologically homogenous fibroblast-like cells and were used at passages 2-5.

The squamous cell carcinoma (UMSCC) cell line derived from patients with head and neck cancer (ATCC™, Manassas, Va.) were maintained in RPMI-1640 medium with 10% FBS. The Human keratinocyte cell line HACAT (ATCC) and the carcinomic human alveolar basal epithelial cell line A549 (ATCC™) were cultured in DMEM with 10% FBS. The diploid lung fibroblasts IMR-90 (ATCC™) were maintained in Minimum Essential Medium (MEM, Invitrogen™) with 10% FBS.

Gene Transfection by Adenoviral Vector

The construction of Indoleamine 2,3-Dioxygenase (IDO) expressing adenoviral vector has been previously described (Li et al., 2004). Recombinant adenoviruses were used to infect human skin fibroblasts at the multiplicity of infection (MOI) of 100. Free viral particles were removed from culture medium 30 hours after infection. The success of infection was determined by fluorescent microscopy using a Motic™ inverted microscope equipped with a fluorescein isothiocyanate (FITC) filter (Motic Instruments™, Richmond, BC, Canada) to view the reporter gene GFP. The expression of IDO was assessed by western blot using anti-human IDO antibody as described previously (Li et al., 2004). The biologic activity of IDO was evaluated by measuring the levels of tryptophan degrading product, kynurenine, present in conditioned medium.

Kynurenine Measurement in Conditioned Media

The levels of kynurenine were measured by a method previously described (Tokikawa et al., 1988). In brief, about 2 ml of conditioned media was collected from the same cell number initiated culture 3 days post transfection. Proteins from conditioned media were precipitated by trichloroacetic acid. After centrifugation to remove precipitated proteins, about 0.5 ml of supernatant was transferred into a new 1.5 ml tube and incubated with equal volume Ehrich's reagent (Sigma™) for 10 minutes at room temperature. The absorption of resultant solution was measured at 490 nm by spectrophotometer within 2 hours. The values of kynurenine in conditioned media were calculated by a standard curve with defined kynurenine concentration (0-20 µg/ml).

Cell Treatments

For collection of conditioned media, fibroblasts were transduced by either none or control mock vector or IDO adenovirus for 30 hours. Viruses were removed by washing with PBS. Fresh DMEM containing 10% FBS and antibiotics were added and cells were continued to be cultured for another 48 hours. Conditioned media from either untreated, mock vector, or IDO adenovirus transduced fibroblasts were then collected. Fibroblasts at 80% confluence were treated with media containing 90% of conditioned media plus 10% fresh media in the presence of 10% FBS. Cells were then harvested after 48 hours and western blot analysis was performed.

In another set of experiments, fibroblasts at 80% confluence were treated with either kynurenine or tryptophan at the indicated concentrations as mentioned in the result section in DMEM containing 2% FBS and antibiotics for 48 hours. Cells were then harvested by trypsinization and western blot analysis was performed.

Similarly, other cells such as synoviocytes, IMR-90, keratinocytes, UMSCC and A549 were treated with kynurenine at concentrations of 12.5 to 150 µg/ml in appropriate media for each cell type as described above for 48 hours. Cells were then harvested for western blot analysis.

Western Blot Analysis

Cells were harvested by Trypsin/EDTA and lysed with cell lysis buffer containing 50 mM Tris-HCl (pH7.40), 150 mM NaCl, 10 mM EDTA, 5 mM EGTA, 1% TritonX-100™, 0.5% Igepal CA-630, 0.025% $NaN_3$ and protease inhibitor cocktail (Sigma™). Cell debris was removed by centrifugation at 20,000×g for 10 minutes. The protein concentration in supernatant was determined using the MicroBCA™ method (Pierce™, Rockford, Ill.). Proteins in supernatant were mixed with protein sample loading buffer (final concentration: 60 mM Tris-HCl (pH 6.80), 2% SDS, 10% glycerol, 1.5% β-mercaptoethanol, 0.002% bromophenol blue) and size fractioned by 10% of SDS-polyacrylamide gel. After proteins were transferred onto nitrocellulose membrane by iBlot™ (Invitrogen Life Technologies™), non-specific binding were blocked with phosphate buffer saline twenty 20 (PBS-T) containing 5% skim milk for 1 hour. The membrane was then incubated with primary antibody overnight. After incubation with a secondary antibody for 1 hour, protein bands were visualized by an enhanced chemiluminescence (ECL™) detection system (Santa Cruz Biotechnology™, Santa Cruz, Calif.). The primary antibodies used in this study were: mouse monoclonal anti-human MMP-1 (R&D Systems™, Minneapolis, Minn.), mouse monoclonal anti-human MMP-3 (R&D System™), rabbit monoclonal anti-human MMP-2 (Epitomics™, Burlingame, Calif.), rabbit polyclonal anti-phospho-MEK1/2 (Ser217/221™) (Cell Signaling Technology™, Danvers, Mass.), rabbit polyclonal anti-phospho-p44/42 MAPK (Thr202/Tyr204) (Cell Signaling Technology™), monoclonal anti-β-actin (Sigma™), and mouse anti-type-1 procollagen (Developmental Studies Hybridoma Bank™, Iowa City, Iowa). The secondary antibodies were either goat anti-mouse IgG (H+L) HPR conjugate or goat anti-rabbit IgG (H+L) HPR conjugate (Bio-rad Laboratory™ (Mississauga, ON, Canada). Secondary antibodies were used at a concentration of 1:3000.

MMP Activity Assay

The activity of MMPs was assessed using a F-FAM/QXL™ 520 fluorescence resonance energy transfer (FRET) peptide as the MMP substrate (SensoLyte 520™ generic MMP assay kit, AnaSpec, Inc.™, Fremont, Calif.) according to the manufacturer's protocol. In brief, cells were treated with or without 50 µg/ml of kynurenine for 48 hours. Conditioned media were collected and incubated with 1 mM of APMA (4-aminophenyl-mercuric acetate, in component C, AnaSpect™) at 37° C. for 3 hrs. After activation MMPs with APMA, 50 µl/well in 96-well plate of conditioned media was mixed with 50 µl of MMP substrate solution.

After incubated at room temperature for 60 minutes, the fluorescence intensity at EX/EM=490 nm/520 nm in each sample including the substrate control were measured using Infinite F500™ fluorescence microplate reader (Tecan Group Ltd™, Morrisville, N.C.).

Phosphorylation Protein Array

Human fibroblasts at 90% confluence were starved in DMEM without FBS overnight followed by the treatment with or without 100 µg/ml of kynurenine for 2 hours. Protein phosphorylation was evaluated using the Human Phospho-Kinase Array™ (R&D System™) according to the manufacturer's instructions. Briefly, capture and control antibodies were spotted in duplicate on nitrocellulose membranes (total 46 kinase phosphorylation sites). Cell lysates (300 µg of total protein per array) were incubated with array overnight. The array was washed to remove unbound proteins, followed by incubation with the cocktail of biotinylated detection antibodies. After incubation with streptavidin-HPR for 30 minutes, signals were visualized by ECL detection system (Santa Cruz™). Blots were analyzed by densitometry, and protein Phosphorylation was Normalized to a Positive Control which was Represented in Each Membrane.

Rabbit Ear Hypertrophic Scar Model and Topical Application of Kynurenine

Female rabbits (New Zealand white) weighing 4.5-5 kg were used for this study. The protocol was reviewed and approved by the University of British Columbia animal care committees. The rabbit ear model of hypertrophic scar was created as described previously (Rahmani-Neishaboor, et al., 2010). Briefly, 2 rabbits were anesthetized by intramuscular injection of ketamine (22.5 mg/kg) and xylazine (2.5 mg/kg) followed by isoflurane gas through tracheal intubation. Four wounds were created down to bare cartilage on the ventral side of each ear using an 8-mm dermal biopsy punch to remove full-thickness sections of skin. Antibiotics were applied on wounds daily until kynurenine treatment was started.

Kynureine in CMC gel (Rahmani-Neishaboor et al., 2010) with a concentration of 500 µg/ml was applied topically to the wounds of the experimental group (0.1 ml per wound) daily for 3 weeks starting at 1 week post wounding. The wounds of the control group were received the treatment with an equal amount of cream alone daily.

Animals were sacrificed on weeks 3 after treatments. Scars (10 mm punch biopsies) were harvested. Each scar was sectioned in two along its longitudinal axis and half of which was processed for routine histological analysis and another half was kept at −80° C. for future use.

Scar elevation was quantified by measuring Scar Elevation Index (SEI) from the H & E stained tissue section. The SEI is a ratio of total height in the wound tissue to the normal tissue below the hypertrophic scar. A SEI of 1 indicates that the scar height is equal to the surrounding unwounded dermis; an SEI>1 indicates a raised hypertrophic scar.

MIT Assay

The effect of kynurenine on human dermal fibroblast proliferation was detected by MTT [3-(4,5-Dimethylthiazol-2-yl)-2,5-diphenyltetrazolium bromide] assay. In brief, 10,000 cells were seeded on a 24 well-plate and incubated with different concentrations of kynurenine for 48 hours. Media were removed and 0.2 ml of MTT (5 mg/ml in DMEM containing 2% FBS) was added. Cells were incubated with MIT for 4 hours. After washing 3 times with PBS, 0.2 ml of DMSO was added to dissolve the crystals. Absorbance was measured at 570 nm.

Measurement of Hydroxyproline Content from Skin Sample:

According to a method previously reported (Gawronskao-Kozak B. et al. 2006), half of 8 mm diameter skin punches were weighed and frozen in −80° C. Skins were homogenized in 2 ml of PBS and stored at 4° C. overnight. The next day, 1 ml of 6N HCl was added and the mixture was heated at 120° C. for 5 hours. 20 µl of cooled samples and 50 µl of chloramine T solution were added to the 96-well plate and incubated at room temperature for 20 minutes. 50 µl of Erlich solution was then added and the mixture was incubated at 65° C. for 15 minutes. Absorbance was read at 570 nm. Hydroxyproline concentration was calculated by a standard curve.

RNA Extraction, cDNA Synthesis and Quantitative RT-PCR

RNA was extracted by Trizol™ (Invitrogen Life Technologies™). Briefly, 1 ml of Trizol™ was added to the homogenized skin tissue. 250 µl of chloroform was added after the mixture was standed at room temperature for 5 minutes. Top aqueous phase was transferred into a new eppendorf tube after centrifugation for 10 minute at 20,000× g. Equal volume isopropanol was added to the aqueous phase and mixed gently. The pellet was washed with 1 ml of 75% ethanol after centrifugation for 20 minutes. RNA was dissolved in DEPC treated $H_2O$ and its concentration was measured by Nanodrop2000™. cDNA was synthesized by cDNA synthesis kit from Roche according to manufacture's introduction using 1 µg of total RNA in each sample. Quantitative real-time PCR for rabbit type-1 α1 collagen, MMP-1 and housekeeper gene β-actin were performed in ViiA7 (Invitrogen™). cDNA samples were added to a PCR reaction master mix containing STBR Green Master Mix™ (Rox) (Roche™, Indianapolis, Ind.). All reactions were performed in duplicate using the following cycle conditions: 1 cycle of 95° C. for 10 minutes, 40 cycles of 95° C. for 15 seconds and 60° C. for 1 minute. The expression level of type-1 α1 collagen and MMP-1 in each sample was normalised to β-actin. RT-PCR primers: rabbit type-1 α1 collagen: 5'-ACAAGGGTGAGACAGGCGAAC-3' (Forward), 5'-GCCGTTGAGTCCATCTTTCCC-3' (Reverse); MMP-1, 5'-TCTGGCCACATCTGCCAATGG-3' (Forward), 5'-AGGGAAGCCAAAGGAGCTGTG-3' (Reverse); β-actin, 5'-AACGAGCGCTTCCGTTGGCCC-3' (Forward), 5'-CTTCTGCATGCGGTCCGCGA-3'(Reverse).

EXAMPLES

Example 1—Indoleamine 2,3-Dioxygenase (IDO) Expression Up-Regulates MMP-1 Expression in Human Dermal Fibroblasts To assess the effect of IDO on MMP-1 expression, a human IDO recombinant adenoviral vector was used for gene transduction in human dermal fibroblasts by a procedure previously reported (Li et al., 2004). Transfection efficiency was evaluated by detecting IDO protein expression and its activity through Western blot analysis and the kynurenine measurement in conditioned media, respectively. As shown in FIG. 1A left panel, the IDO protein was expressed in IDO adenovirus-transduced fibroblasts, but undetectable in control and mock adenovirus-transduced fibroblasts. The level of kynurenine, an index for IDO activity, was significantly higher in IDO adenovirus-transduced fibroblasts (14.3±0.46 µg/ml, n=3) compared to those in untransduced or mock-transduced controls (Figure A, right panel).

The expression of MMP-1 in control, mock-transduced and IDO-expressing fibroblasts was examined by using Western blot analysis. As shown in FIG. 1B, there was a more than nine fold increase in MMP-1 expression in IDO-expressing fibroblasts (12.56±2.37, n=3) as compared to those in mock-transduced (1.37±0.59, n=3) and untreated control fibroblasts (1±0, n=3). This finding suggests that up-regulation of MMP-1 expression in IDO-expressing fibroblasts is not due to adenovirus infection, since the mock-transduced fibroblasts showed no significant difference in MMP-1 expression from the untreated fibroblasts.

IDO is an intracellular enzyme that converts tryptophan into kynurenine. Therefore, it must be clarified whether the effect of MMP-1 stimulation in IDO-expressing fibroblasts is due to the IDO protein itself or to tryptophan metabolites. To address this, conditioned media from both IDO-expressing fibroblasts and controls were collected after 48 hours. A combination of 90% collected conditioned media and 10% fresh media was then used to treat dermal fibroblasts. Cells were harvested 48 hours after treatment. As shown in FIG. 1C, a significant increase in MMP-1 expression was observed in cells treated with conditioned media from IDO-transduced fibroblasts (2.06±0.62, n=3) as compared to those in either mock-transduced (1.16±0.31, n=3) or untreated control fibroblasts (1±0, n=3). This result suggests that a factor or factors in conditioned media from IDO adenovirus infected fibroblast rather than intracellular IDO protein is responsible for an increased level of MMP-1 expression in fibroblasts.

Example 2—Kynurenine but not Depletion of Tryptophan Induces MMP-1 Expression in Human Dermal Fibroblasts IDO is an enzyme converting tryptophan into kynurenine. To examine what factor (either depletion of tryptophan or increase of kynurenine) is responsible for IDO up-regulation of MMP-1 expression. To examine what factor is responsible for IDO up-regulation of MMP-1 expression, fibroblasts were grown in either tryptophan-depleted cultured media or regular media with various concentrations of kynurenine. Cells were then evaluated for MMP-1 expression by western blotting. As shown in FIG. 2C, there was no significant difference in the expression of MMP-1 between fibroblasts grown in the presence of 25 μg/ml tryptophan or in the tryptophan-depleted cultured media. However, the MMP-1 expression was significantly increased in response to different doses (25-150 μg/ml) of kynurenine (FIG. 2A and FIG. 2B). These findings suggest that the presence of kynurenine, but not tryptophan depletion, contributes to the up-regulation of MMP-1 in IDO-expressing cells. Furthermore, we found that as little as 12.5 μg/ml of kynurenine could stimulate MMP-1 expression in dermal fibroblasts (data not shown). This concentration of kynurenine is similar to that detected in conditioned media from IDO expressing fibroblasts (FIG. 1A right panel). The stimulation of MMP-1 in fibroblasts is thus clearly specific to kynurenine as the addition of various concentration of tryptophan with a similar structure failed to increase the expression of MMP-1 in dermal fibroblasts (FIG. 2D).

Figure 2:
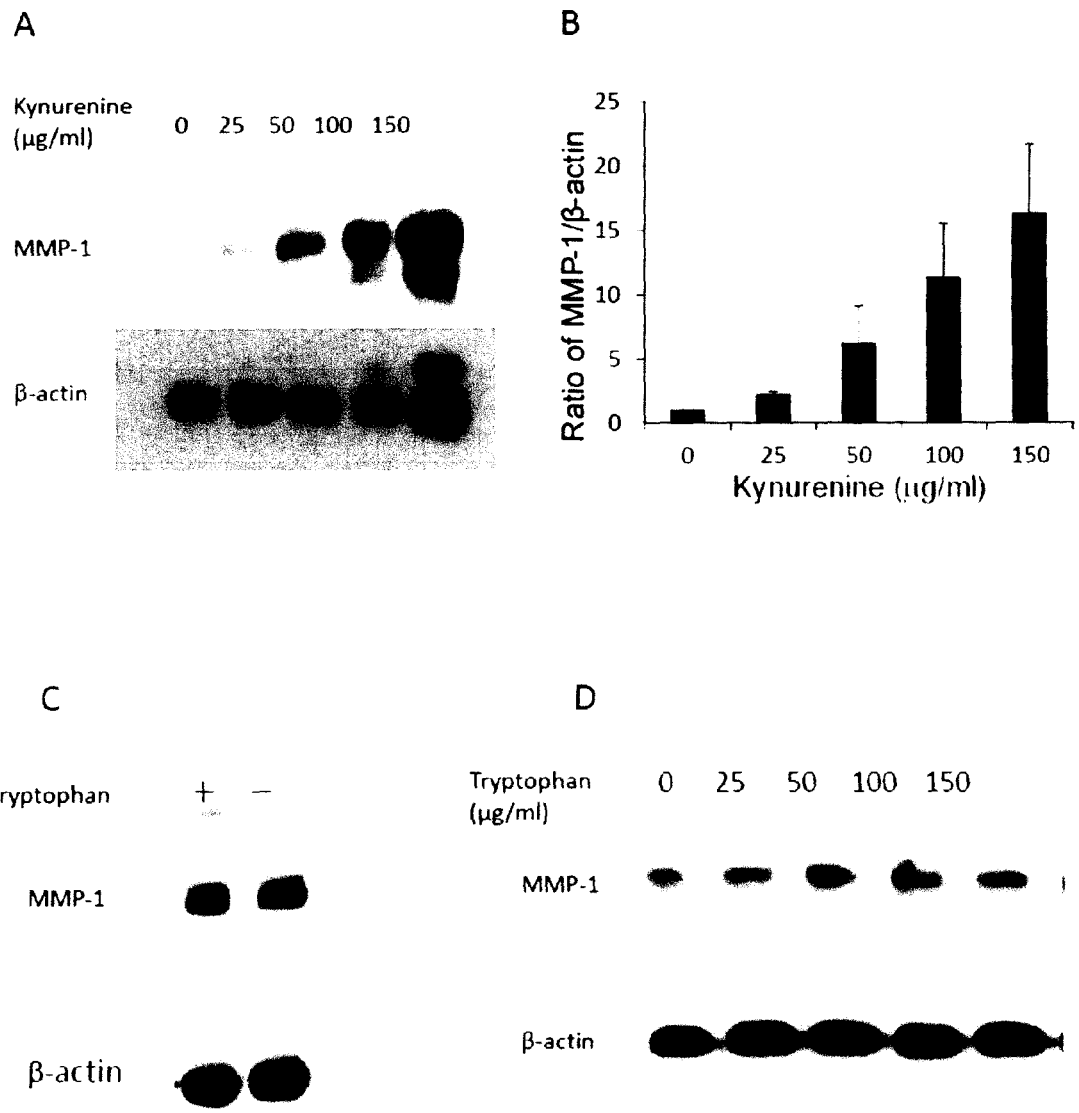
FIG. 2: Effects of Kynurenine and tryptophan on MMP-1 expression in human dermal fibroblasts. Panels A and B show dermal fibroblasts that were cultured in the presence of various concentrations of kynurenine for 48 hours, when the cells were harvested and lysed, before Western blotting was performed, showing the ratio of MMP-1 to 3-actin is presented in panel B. Panel C shows dermal fibroblasts that were cultured in the presence or absence of tryptophan (25 mg/ml) for 48 hrs, when cells were harvested and lysed, and MMP-1 expression was evaluated by Western blotting. Panel D shows fibroblasts that were cultured in the presence of different concentrations of tryptophan for 48 hours, when the expression of MMP-1 was evaluated by Western blotting. β-actin was used for a loading control in all panels.
Figure 3:
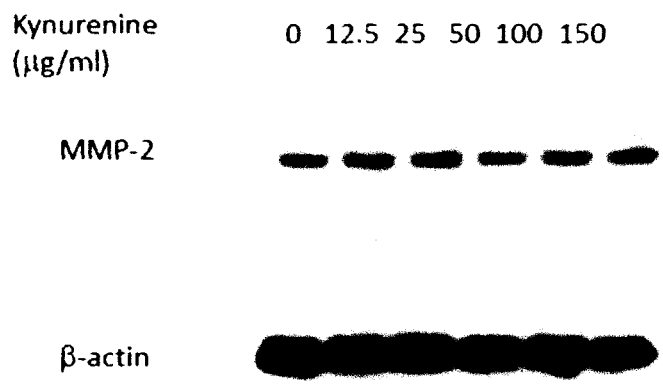
FIG. 3: Effects of kynurenine on MMP-2 and -3 expression in human dermal fibroblasts—shows dermal fibroblasts that were cultured in the presence of various concentrations of kynurenine for 48 hours, before cells were harvested and lysed, and Western blotting was performed using either a rabbit monoclonal anti-human MMP-2 antibody (Panel A) or a mouse monoclonal anti-MMP-3 antibody (Panel B). Panel C shows the ratio of MMP-3 expression to b-actin for three independent experiments. β-actin was used for a loading control in all experiments.
Figure 3:
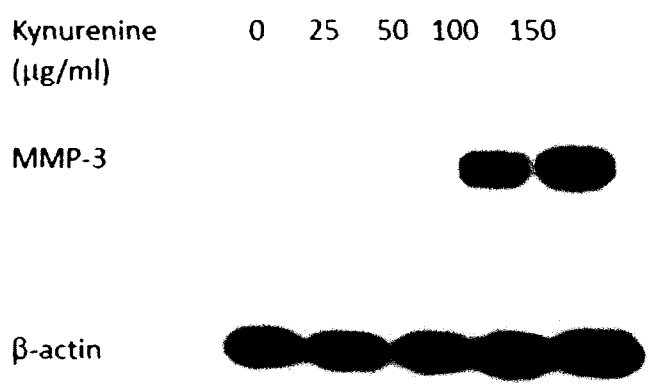
Figure 3:
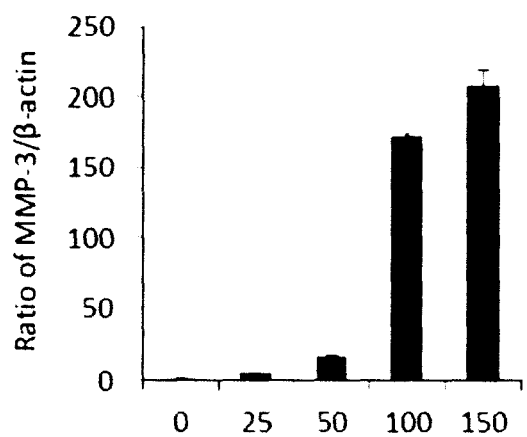
Figure 4:
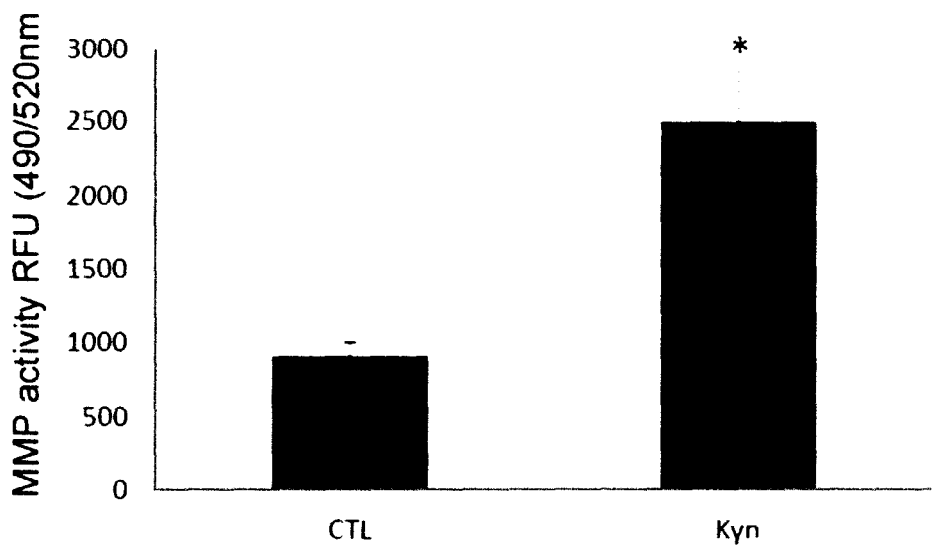
FIG. 4: Detect the activity of MMPs in conditioned media of human dermal fibroblasts using SensoLyte 520 generic MMP assay fluorimetric kit—shows fibroblasts that were cultured in the presence of (Kyn) or absence (CTL) of 50 μg/ml of kynurenine for 48 hours, when cell conditioned media was collected, then after centrifugation at 1000×g for 10 minutes, supernatant was used to detect the activity of MMPs according to manufacture's instructions (media were incubated with 1 mM APMA at 37° C. for 3 hrs. 50 μl/well of MMP containing sample was then mixed with 50 μl of MMP substrate solution and medium from before cell culture was mixed with 50 μl of MMP substrate solution and used as a substrate control and after incubation 1 hour, the fluorescence intensity at EX/EM=490 nm/520 nm were measured). The activity of MMPs are represented as relative fluorescence unit (RFU). Data was expressed as mean±SD (n=3). * indicates P<0.05.

Example 3—Effects of Kynurenine on MMP-2 and -3 Expression in Dermal Fibroblasts To investigate whether kynurenine also affects the expression of other MMPs, we treated dermal fibroblasts with kynurenine at similar concentrations to those used in FIG. 2. Western blotting was used to detect MMP-2 and -3 expression using untreated cells as controls. As shown in FIG. 3A, there was no significant difference in MMP-2 expression between kynurenine-treated and untreated fibroblasts. However, under similar conditions, kynurenine treatment significantly increased MMP-3 expression in dermal fibroblasts in a dose-dependent manner (FIG. 3B/3C). Furthermore, to test whether the increased levels of MMPs in kynurenine-treated fibroblasts were followed by increased MMP activity, conditioned media from fibroblasts in the presence or absence of 50 μg/ml of kynurenine were collected 48 hours after treatment. The MMP activity in the conditioned media was detected by a SensoLyte 520™ generic MMP assay kit using a 5-FAM/QXL™520 fluorescence resonance energy transfer (FRET) peptide as a MMP substrate. As shown in FIG. 4, the mean activity of MMPs in conditioned media from the kynurenine treated fibroblast was significantly higher than in the control media. This indicates that the increased MMPS in fibroblasts treated by kynurenine have enzymatic activity.

Figure 5:
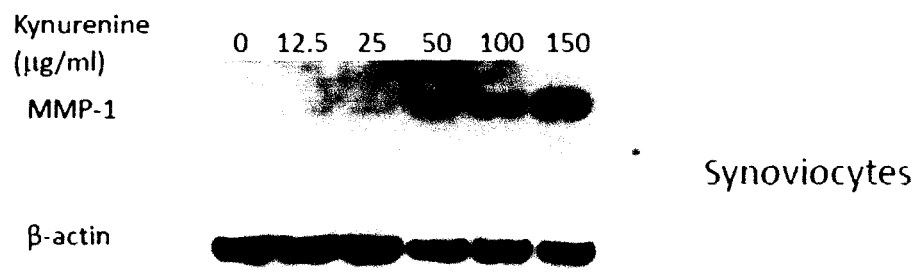
FIG. 5: Effects of kynurenine on MMP-1 expression in different types of mesenchymal cells—shows cells that were cultured and treated with kynurenine at concentrations of 12.5 to 150 μg/ml for 48 hours and MMP-1 expression was analysed by Western blotting and β-actin was used as a loading control in all experiments. Panel A shows MMP-1 expression in synoviocytes. Panel B shows MMP-1 expression in lung fibroblast cell line IMR-90.
Figure 5:
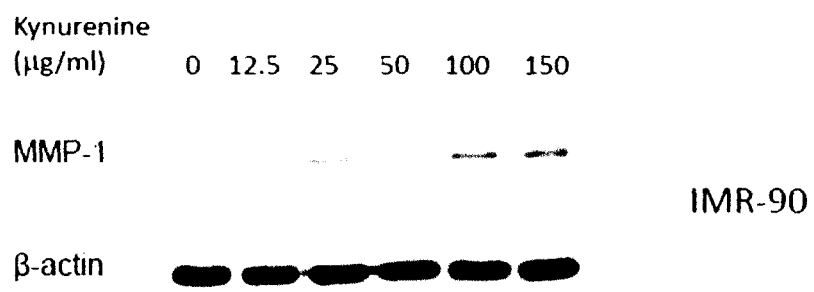
Figure 6:
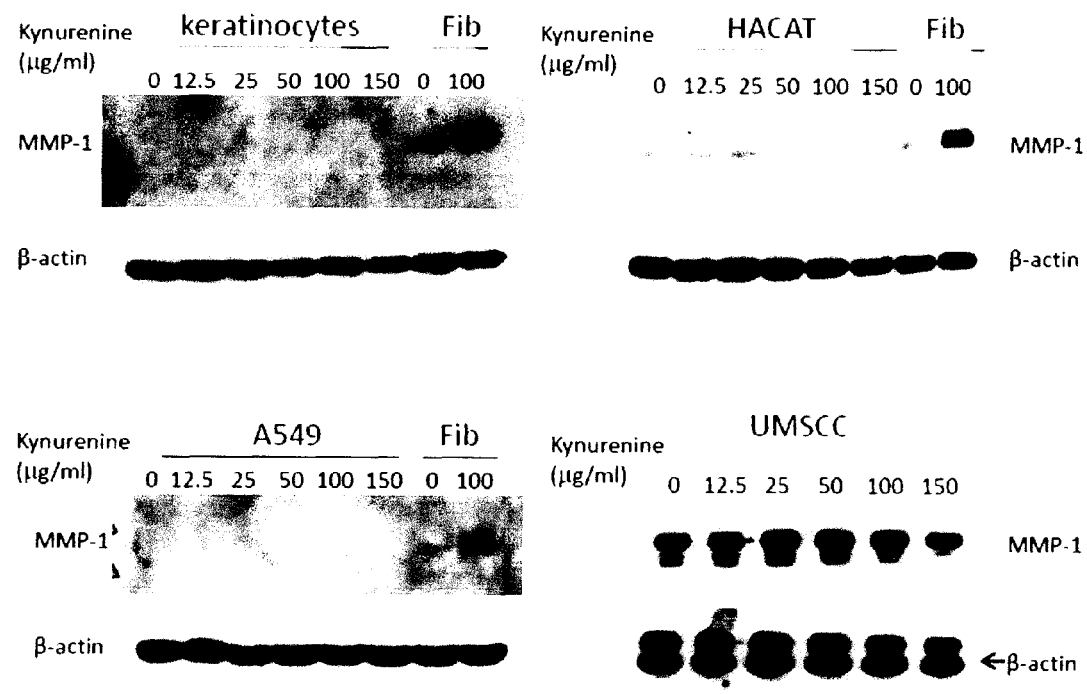
FIG. 6: Effects of kynurenine on MMP-1 expression in different types of epithelial cells—shows cells were cultured and treated with kynurenine at concentrations of 12.5 to 150 μg/ml for 48 hours and MMP-1 expression was analysed by western blotting and β-actin was used as a loading control in all experiments, where the top panels and bottom left panel, show fibroblast lysates from either untreated or kynurenine treated that were used as negative and positive controls, respectively.

Example 4—Mesenchymal and Epithelial Cells Respond Differently to Kynurenine Treatment To determine what types of cells are sensitive to kynurenine-induced MMP-1 expression, both mesenchymal cells (such as an immobilized lung fibroblast cell line IMR-90 and fibroblast-like synoviocytes) and epithelial cells (such as lung epithelial carcinoma cell line A549, primary dermal keratinocytes, human immobilized keratinocyte cell line HACAT, and head and neck squamous cell carcinoma cell line UMSCC) were used. As with the dermal fibroblasts, MMP-1 expression in synoviocytes and IMR-90 were up-regulated by kynurenine treatments at concentrations of 12.5 μg/ml to 150 μg/ml, as shown in FIG. 5. However, the expression of MMP-1 in all epithelial cells tested, including dermal keratinocytes, HACAT, A549 and UMSCC, did not significantly differ from the untreated controls in response to the various concentration of kynurenine (FIG. 6). These results suggest that there is a difference between mesenchymal and epithelial cells in response to kynurenine-stimulating MMP-1 expression.

Figure 7:
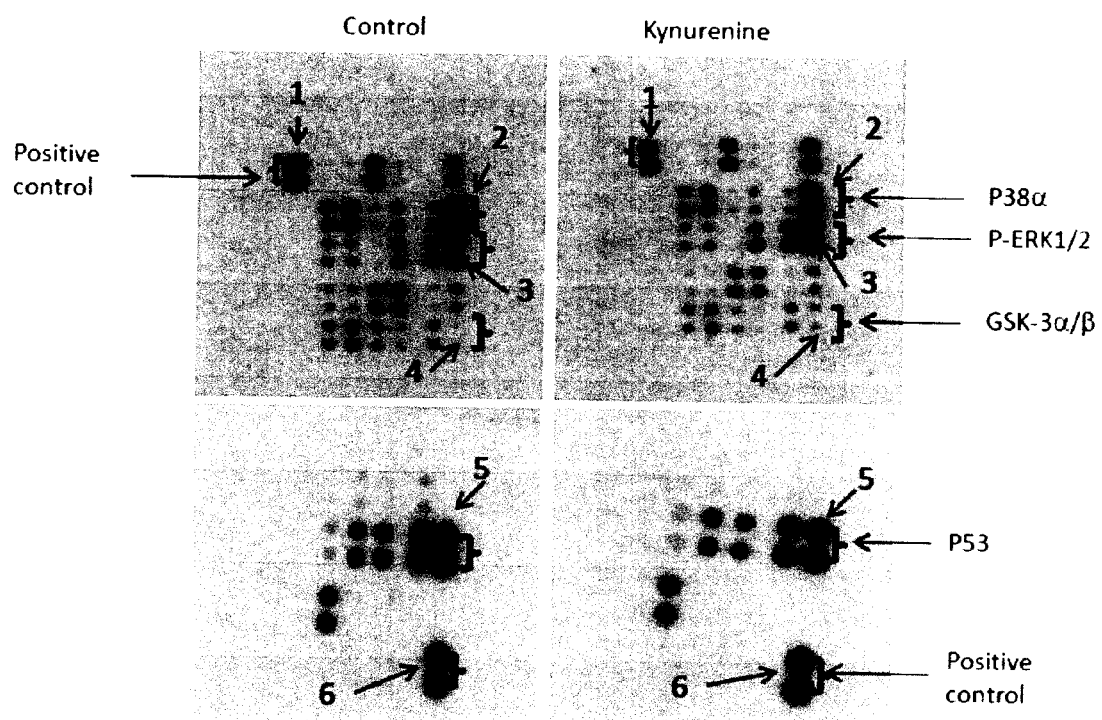
FIG. 7: Kynurenine stimulates ERK1/2 phosphorylation in human dermal fibroblasts—shows dermal fibroblasts that were cultured in the absence or presence of 100 g/ml of kynurenine for 60 minutes, then cells were harvested and lysed with cell lysis buffer, before an antibody array was performed using a human phospho-kinase array kit (R & D System™), with spot 1, positive control; spot 2, phospho-P38α; spot 3, phosphor-ERK1/2; spot 4, phosphor-GSK-3α/β; spot 5, phosphor-P53; spot 6, positive control.

Example 5—Identification of the Phosphorylated Signal Molecules by Phospho-Kinase Array in Cells Treated with Kynurenine To determine the possible mechanism of kynurenine up-regulated MMP-1 expression in dermal fibroblasts, we analyzed the activation of multiple serine, threonine or tyrosine kinases, using a phosphor-kinase array. This array gives the possibility of simultaneously detecting the activation status of 46 different protein kinases and their downstream transcript factors. As shown in FIG. 7, after 1 hour of treatment in dermal fibroblasts with kynurenine, extracellular signal-regulated kinases 1/2 (ERK1/2) was activated.

Figure 8:
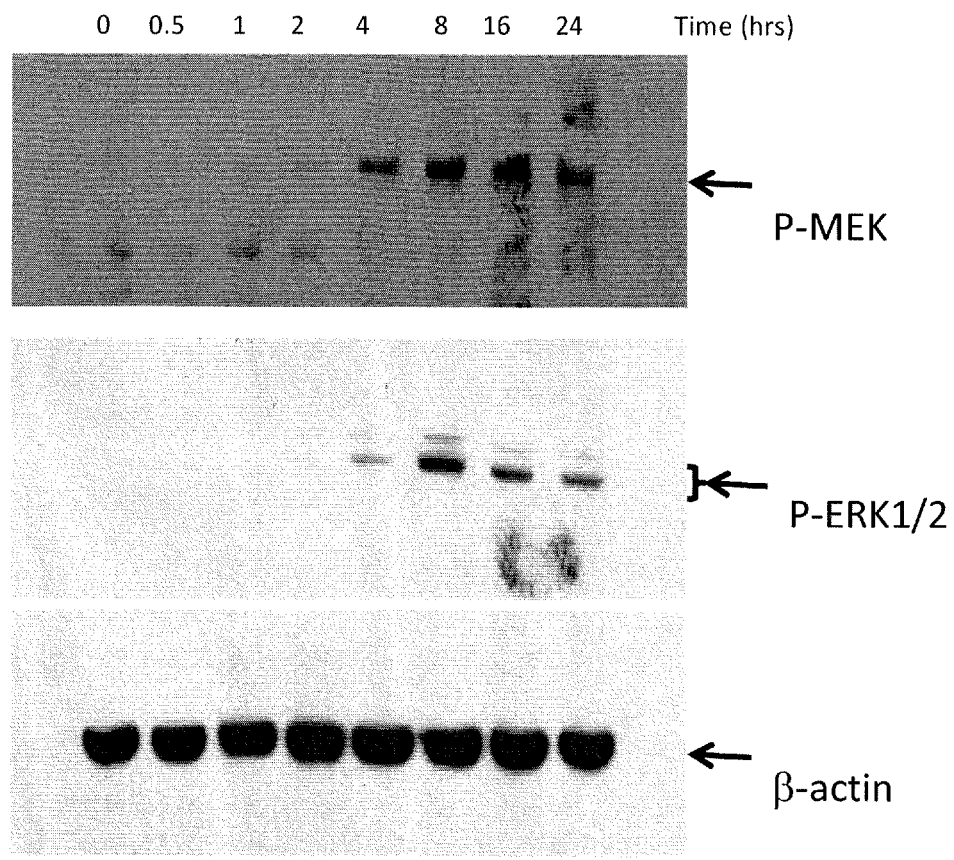
FIG. 8: Kynurenine stimulation of MEK and ERK1/2 phosphorylation in human dermal fibroblasts—shows dermal fibroblasts that were cultured in the presence of 100 μg/ml of kynurenine at indicated time points, when cells were harvested and lysed, before Western blotting was performed by using either phosphorylated-MEK or phosphorylated-ERK1/2 antibody (β-actin was used as a loading control).

To confirm these results from the phospho-kinase array, dermal fibroblasts were treated with 100 μg/ml of kynurenine at different times. Immunoblotting analysis, using a different antibody from those placed on the array, was then used to detect the phosphorylation of ERK1/2 and its upstream molecule mitogen-activated protein/extracellular signal-regulated kinase kinase (MEK). As shown in FIG. 8, ERK1/2 was phosphorylated in cells treated with kynurenine. The result was further confirmed by detection of the ERK1/2 upstream signal molecule MEK phosphorylation in cells treated with kynurenine (FIG. 8). Both ERK1/2 and MEK showed similar patterns of activation, with a peak at 8 hours following kynurenine treatments (FIG. 8).

Figure 9:
FIG. 9—Addition of MEK or ERK1/2 phosphorylation inhibitors negates the effect of kynurenine-stimulating MMP-1 expression in dermal fibroblasts. Panel A: shows dermal fibroblasts were cultured in the absence or presence of 100 μg/ml kynurenine with or without various concentration of PD98059. Panel B: shows dermal fibroblasts were cultured in the absence or presence of 100 μg/ml kynurenine with or without 30 μM of PD98059 (ERK1/2 inhibitor), 30 μM of U0126 (MEK inhibitor) or 10 μM of U0126. MMP-1 expression was detected by Western blot (β-actin was used as a loading control for all experiments).
Figure 9:

Example 6—Addition of Inhibitors for MEK-ERK1/2 Phosphorylation Negates the Effects of Kynurenine Stimulated MMP-1 Expression in Dermal Fibroblasts In another set of experiments, we tested whether the activation of the MEK-ERK1/2 MAPK pathway by kynurenine is associated with kynurenine-stimulating MMP-1 expression in dermal fibroblasts. To do this, we examined the effects of inhibitors of either MEK or ERK1/2 phosphorylation on kynurenine-stimulating MMP-1 expression. As shown in FIG. 9A, the addition of PD98059, a specific inhibitor for ERK1/2 activation effectively prevented the stimulatory effect of kynurenine on MMP-1 expression, in a dose-dependent manner. Similarly, treatment of cells with to M and 30 µM of U0126, a specific inhibitor for MEK activation, also significantly reduced the up-regulation of MMP-1 expression by kynurenine (FIG. 9B). These results demonstrate that the activation of the MEK-ERK1/2 signaling pathway contributes to the up-regulation of MMP-1 expression induced by kynurenine in dermal fibroblasts.

Figure 11:
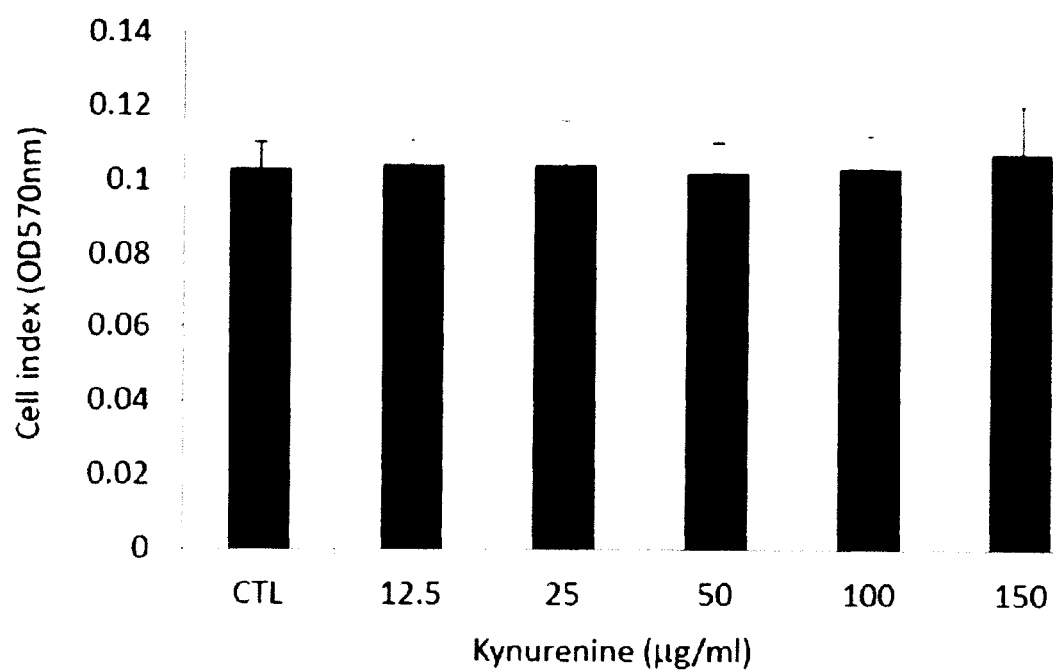
FIG. 11—Effect of kynurenine on fibroblast proliferation—shows human dermal fibroblasts were cultured in the presence of indicated concentrations of kynurenine for 48 hours. MT cell proliferation assay was performed as described herein, with cell proliferation indicated as cell index (OD570 nm) in the MTT assay.

Example 7—Effects of Kynurenine on Collagen Expression in Dermal Fibroblasts and Fibroblast Proliferation Before studying its anti-fibrotic role in vivo, kynurenine was tested for its effect on collagen expression and cell proliferation. As shown in Figure to (top), the addition of kynurenine 25-150 µg/ml remarkably decreases the expression of type 1 procollagen. However, it had no significant effect on fibroblast proliferation, even when the cells were cultured at concentrations up to 150 µg/ml of kynurenine (FIG. 11). Also, testing of the kynurenine analogues/metabolites, kynurenic acid and xanthurenic acid, demonstrate that these compounds are also effective at inhibiting expression of type 1 procollagen (Figure to (bottom)).

Figure 12:
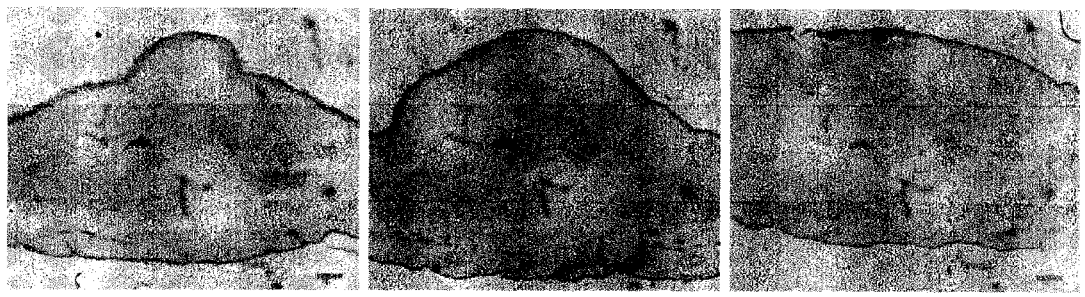
FIG. 12—Clinical appearance and histology of wound and scars—shows rabbit ear wounds that were treated daily with either nothing (CTL), CMC gel alone (Gel), or 50 μg of kynurenine (Kyn) in 0.1 ml of CMC gel started from day 8 for a total of 3 weeks. Panel A: shows the microscopic histology of wounds receiving either nothing (CTL), CMC gel (Gel) or kynurenine in CMC gel (Kyn) on Day 28 at magnification ×25. Panel B: shows the scar elevation index (SEI) as measured (Mean±SD of SEI for untreated, CMC gel, and kynurenine in CMC gel-treated wounds) * shows a significant difference between kynurenine-treated and untreated controls (P<0.001); ** shows a significant difference between kynurenine and CMC gel control groups (P<0.01). Panel C: shows Massons' trichrome stained full-thickness skin sections from either untreated skin wound (left panels), cream treated skin wound (middle panels), or kynurenine treated wound (right panels) at both at magnification ×25 and ×100. Panel D: shows the total hydroxyproline content of skins from either untreated wounds (total 4 wounds), cream treated wounds (total 4 wounds), or kynurenine treated wounds (total 8 wounds)—* indicates p<0.01.
Figure 12:
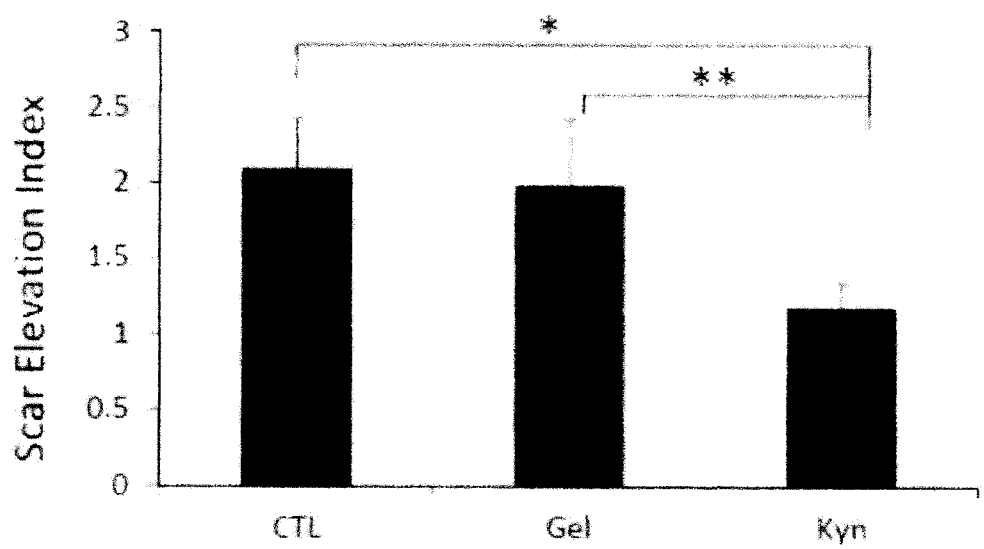
Figure 12:
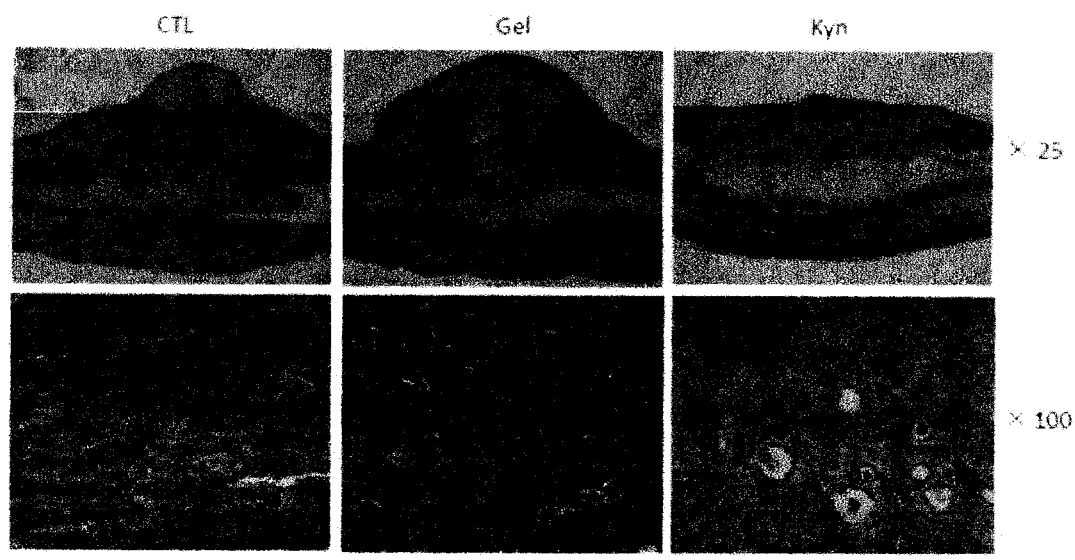
Figure 12:
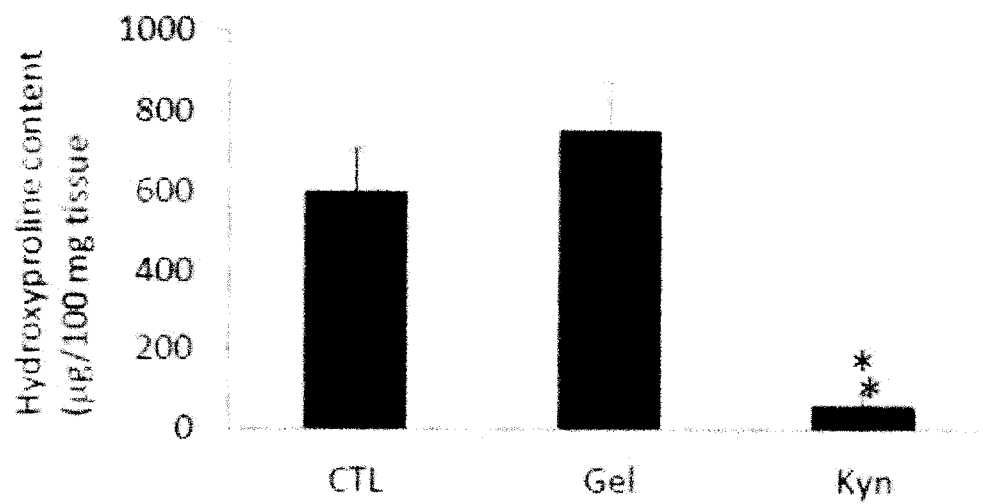

Example 8—Topical Application of Kynurenine on Rabbit Ear Wounds Reduces Scarring Since treatment of dermal fibroblasts with kynurenine showed an increase in both the MMP-1 and -3 expression as well as a decrease in type-1 procollagen expression, we were interested to know whether kynurenine can be used as an anti-fibrotic agent for the treatment or prevention of hypertrophic scarring. To achieve this, as described previously (Rahmani-Neishaboor et al., 2010; Kloeters et al., 2007; Xie et al., 2008), a rabbit ear hypertrophic scar model was used. Wounds were treated daily with 0.1 ml of carboxymethyl cellulose (CMC) gel containing 50 µg of kynurenine for three weeks starting at day 8 post-wounding. The dose of 50 mg kynurenine per wound was matched with that used in an in vitro system with an optimum outcome. The result showed no significant difference to wound closure in kynurenine-treated wounds as compared to that of either untreated or CMC gel treated controls (data not shown). However, as shown in FIG. 12A, significantly less scarring was seen in wounds treated with kynurenine than either non-treated wounds or the vehicle-only control wounds after three weeks. The average scar elevation index (SEI) was significantly reduced in the kynurenine-treated group ($1.172\pm0.156$, n=8) as compared to the vehicle-only control group ($1.978\pm0.442$, n=4) and the untreated group ($2.098\pm0.324$, n=4, $p<0.001$) (FIG. 12B). Massons' trichrome staining for collagen revealed a significant reduction in collagen content in wounds treated with kynurenine, compared to those wounds receiving either no treatment or gel alone (FIG. 12C). Consistent with this finding, the hydroxyproline content (used as an index for tissue collagen content) was significant lower in wounds treated with kynurenine compared to those wounds receiving either no treatment or gel alone (FIG. 12D).

Figure 13:
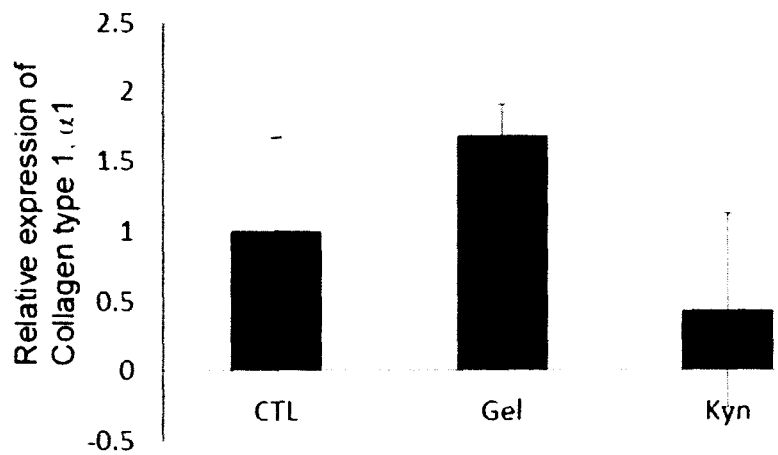
FIG. 13—Topical application of kynurenine decreases type-1 α1 collagen and increases MMP-1 expression in rabbit ear skin—shows wounds in rabbit ear that were treated with either nothing (CTL) or gel alone (Gel) or kynurenine plus gel (Kyn) as described above, where skin wounds were used to extract total RNA by Trizol™ and 1 μg of RNA was used to synthesize cDNA for quantitative RT-PCR for type-1 α1 collagen, MMP-1 and β-actin. Panel A: shows the relative expression level of type-1 α1 collagen in rabbit ear skin tissue. Panel B: shows the relative expression level of MMP-1 in rabbit ear skin tissue—* indicates p<0.05.

Finally, we demonstrated that topical application of kynurenine in a rabbit ear fibrotic model decreased the expression of type-1 α1 collagen and increased the expression of MMP-1, as compared to those in wounds received either no treatment or gel alone (FIG. 13). These results further support the supposition that kynurenine could potentially be used as an anti-fibrotic factor for treating hypertrophic scarring and even keloid, as frequently seen in patients with burn injuries or surgical incisions.

Figure 14:
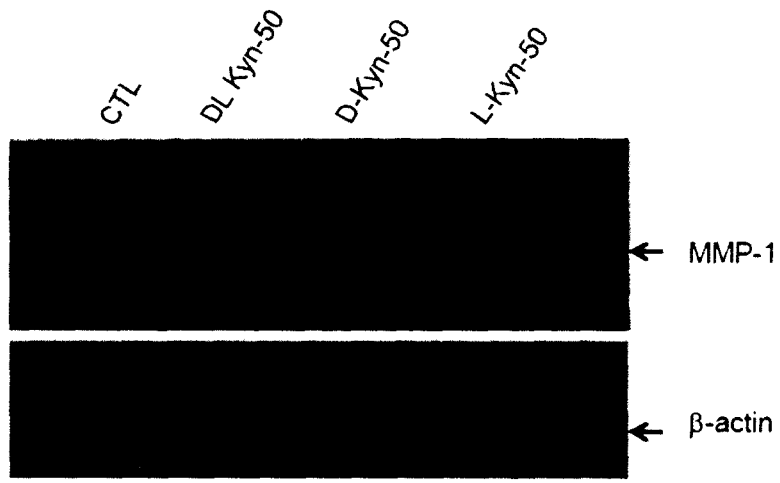
FIG. 14—Effect of kynurenine isoform on MMP-1 expression in human dermal fibroblasts—shows dermal fibroblasts that were cultured in the absence (CTL) or presence of 50 μg/ml either DL-kynurenine (DL-Kyn) or D-kynurenine (D-Kyn) or L-kynurenine (L-Kyn) for 48 hours, at which time cells were harvested and lysed in protein lysis buffer (50 μg total protein was loaded on 10% SDS acrylamide gel) before Western blotting was performed with anti-human MMP-1 antibody, with β-actin as a loading control, which shows that all kynurenine isoforms tested increase MMP-1 expression in dermal fibroblasts, however, L-kynureine seems have more activity compared to other two isoforms.

Example 9—Effect of Kynurenine Isoforms on MMP-1 Expression in Human Dermal Fibroblasts Different isoforms of kynurenine were tested for their ability to affect MMP-1 expression. Isoforms tested were DL-kynurenine (DL-Kyn) or D-kynurenine (D-Kyn) and L-kynurenine (L-Kyn). The result showed that all isoforms increase the MMP-1 expression in dermal fibroblasts, however, L-kynurenine seems to have more activity compared to other two isoforms—see FIG. 14.

Figure 15:
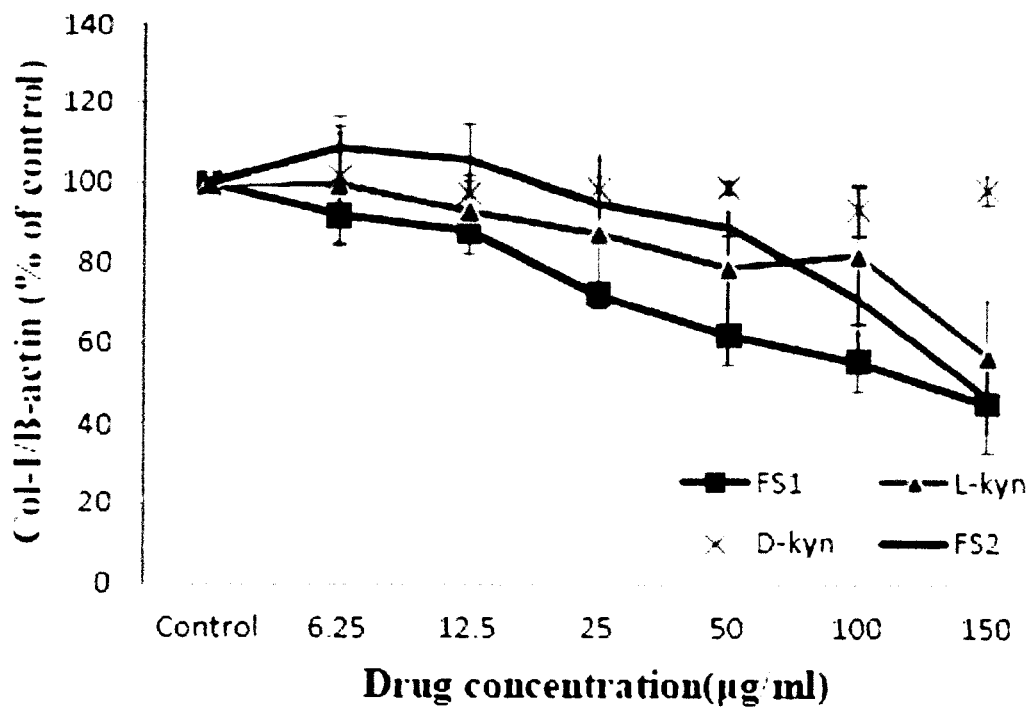
FIG. 15—Effects of kynurenine (FS1) analogues on collagen expression in human dermal fibroblasts—shows dermal fibroblasts that were treated with various concentration of either DL-kynurenine (FS1), L-kynurenine, D-kynurenine or kynurenic acid (FS2) and the corresponding collagen expression in mRNA levels as detected by real-time PCR, with β-actin as a loading control.

Example 10—Effects of Different Kynurenine Isoforms/Analogues on Collagen Expression in Human Dermal Fibroblasts Dermal fibroblasts were treated with either FS-1 (DL-kynurenine) or D-kynurenine or L-kynurenine or FS-2 (kynurenic acid) as shown in FIG. 15. Type-1, α1-collagen expression was detected by real-time PCR. Results indicate that these isoforms/analogues have similar efficacy in reducing collagen expression.

Figure 16:
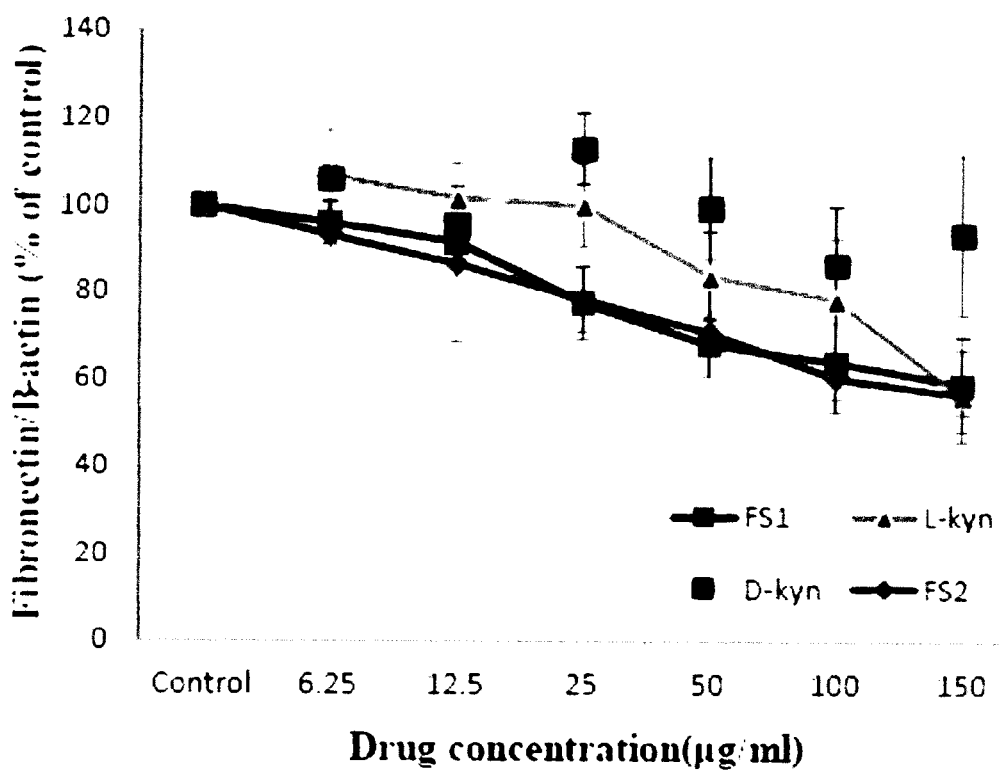
FIG. 16—Effects of kynurenine (FS1) analogues on fibronectin expression in human dermal fibroblasts—shows dermal fibroblasts were treated with various concentration of either DL-kynurenine (FS1), L-kynurenine, D-kynurenine or kynurenic acid (FS2) and the corresponding fibronectin expression in mRNA levels as detected by real-time PCR, with β-actin as a loading control.

Example 11—Kynurenine and its Metabolites Down-Regulate Fibronectin Expression in Cultured Fibroblasts Dermal fibroblasts were treated with various concentration of either DL-kynurenine (FS1), L-kynurenine, D-kynurenine or kynurenic acid (FS2) as shown in FIG. 16. The expression of fibronectin was detected by real-time PCR. Results demonstrate that kynurenine, DL-kynurenine, and L-kynurenine are all capable of down-regulating fibronectin expression, indicating that kynurenine metabolites may be also suitable for prevention or treatment of fibroproliferative disorders.

Figure 17:
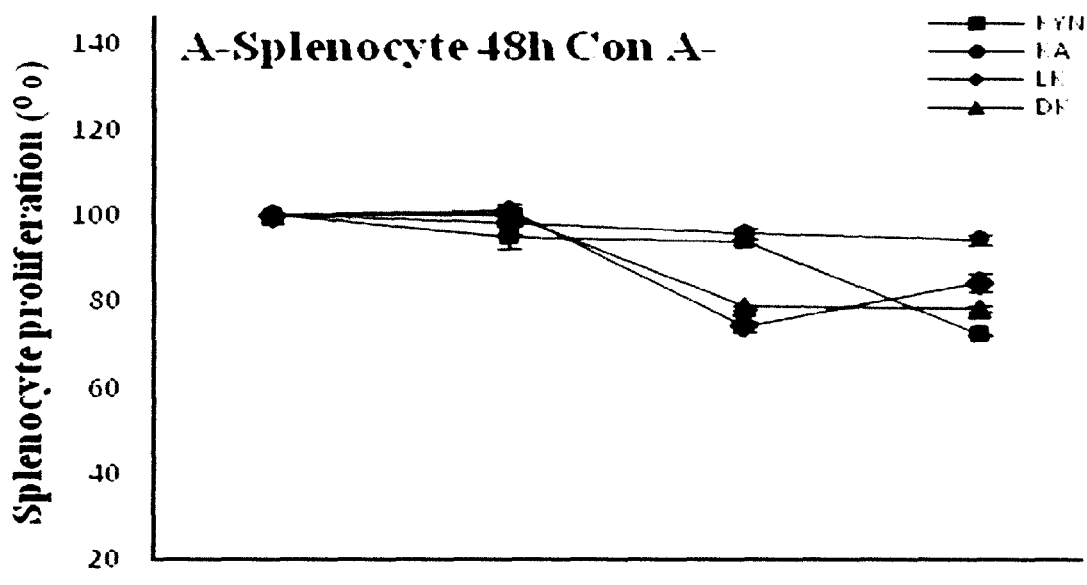
FIG. 17—Comparing the suppressive effect of 50, 100, 150 μg/mL Tryptophan metabolites (FS1, LK, FS2, DK) on ConA-simulating splenocyte proliferation—shows that there was almost a 5-fold reduction in splenocyte proliferation following treatment with 100 and 150 μg/ml of D-Kyn, L-Kyn, DL-Kyn (FS-1) and Kynurenic acid (FS2) after 96 hours (P<0.05), although splenocytes proliferation significantly reduced about 2-fold by D-Kyn, L-Kyn and DL-Kyn at 100 and 150 μg/ml after 48 hours, but FS2 showed less of an effect on proliferation.
Figure 17:
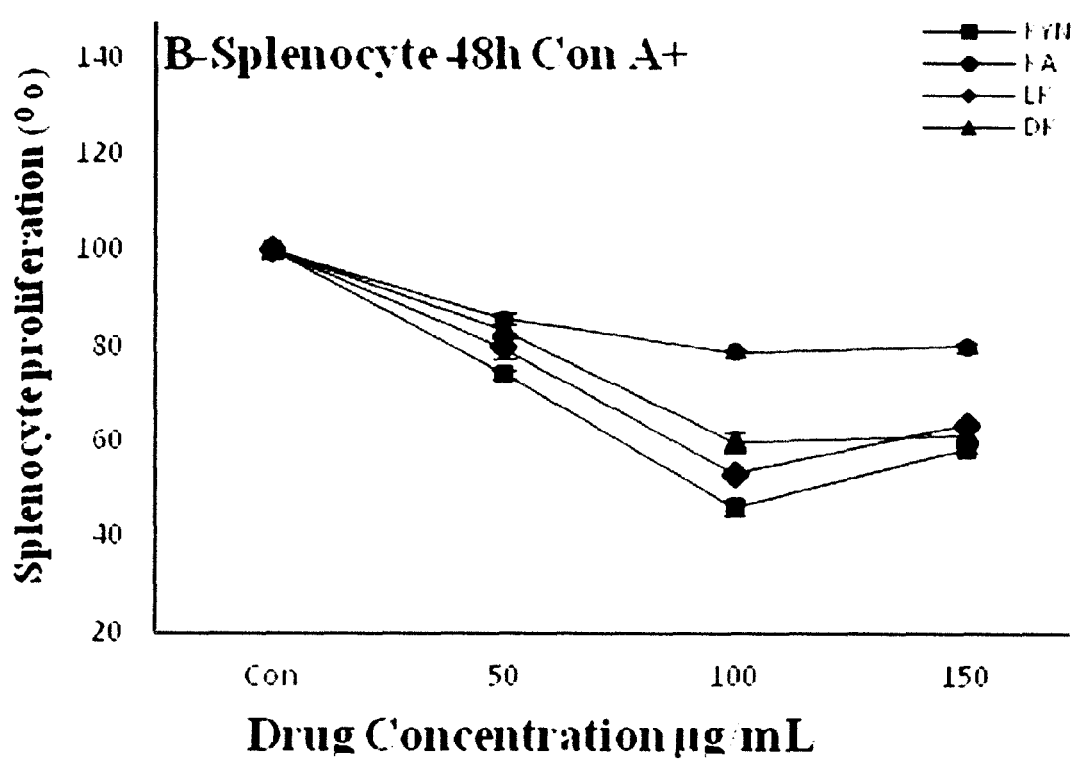
Figure 17:
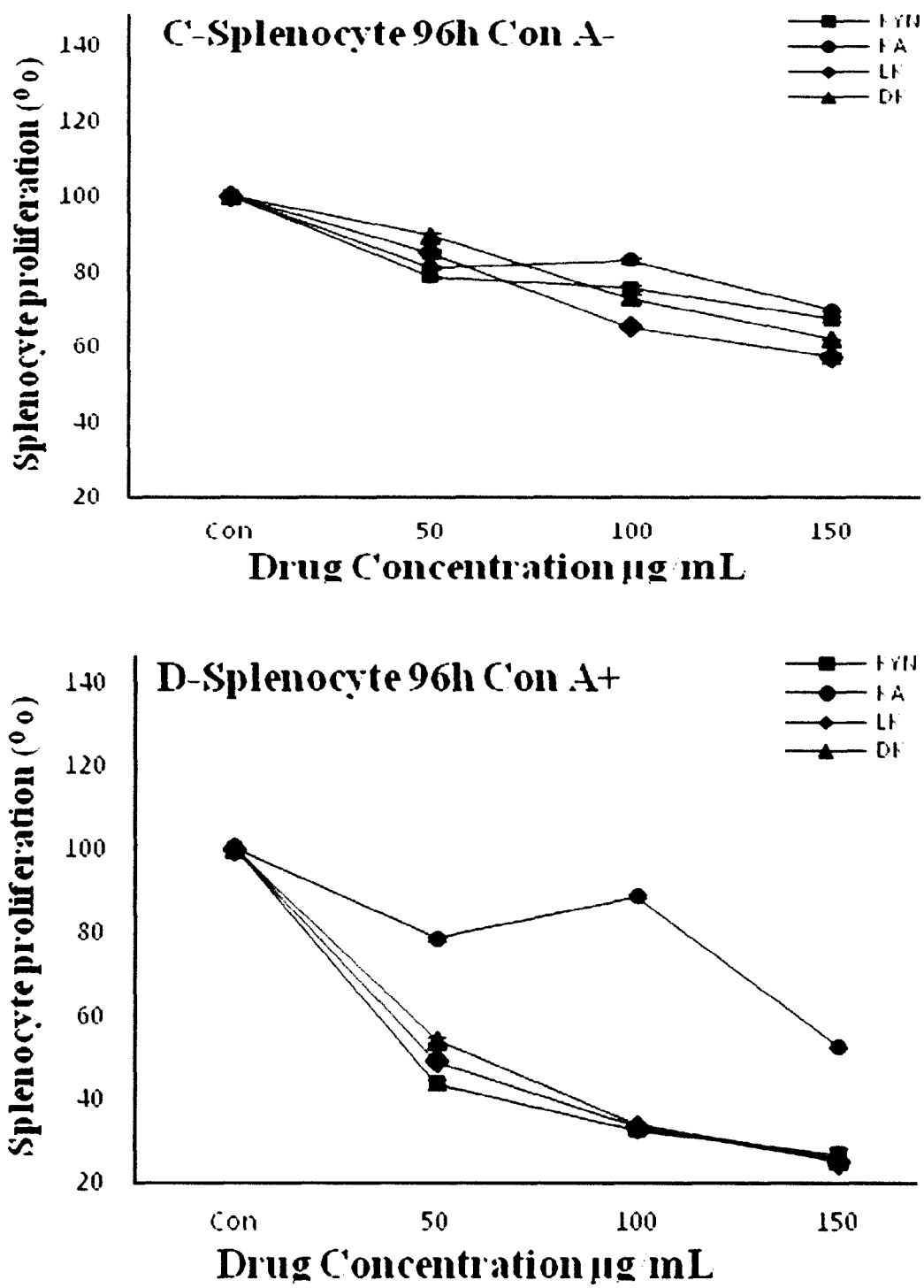
Figure 18:
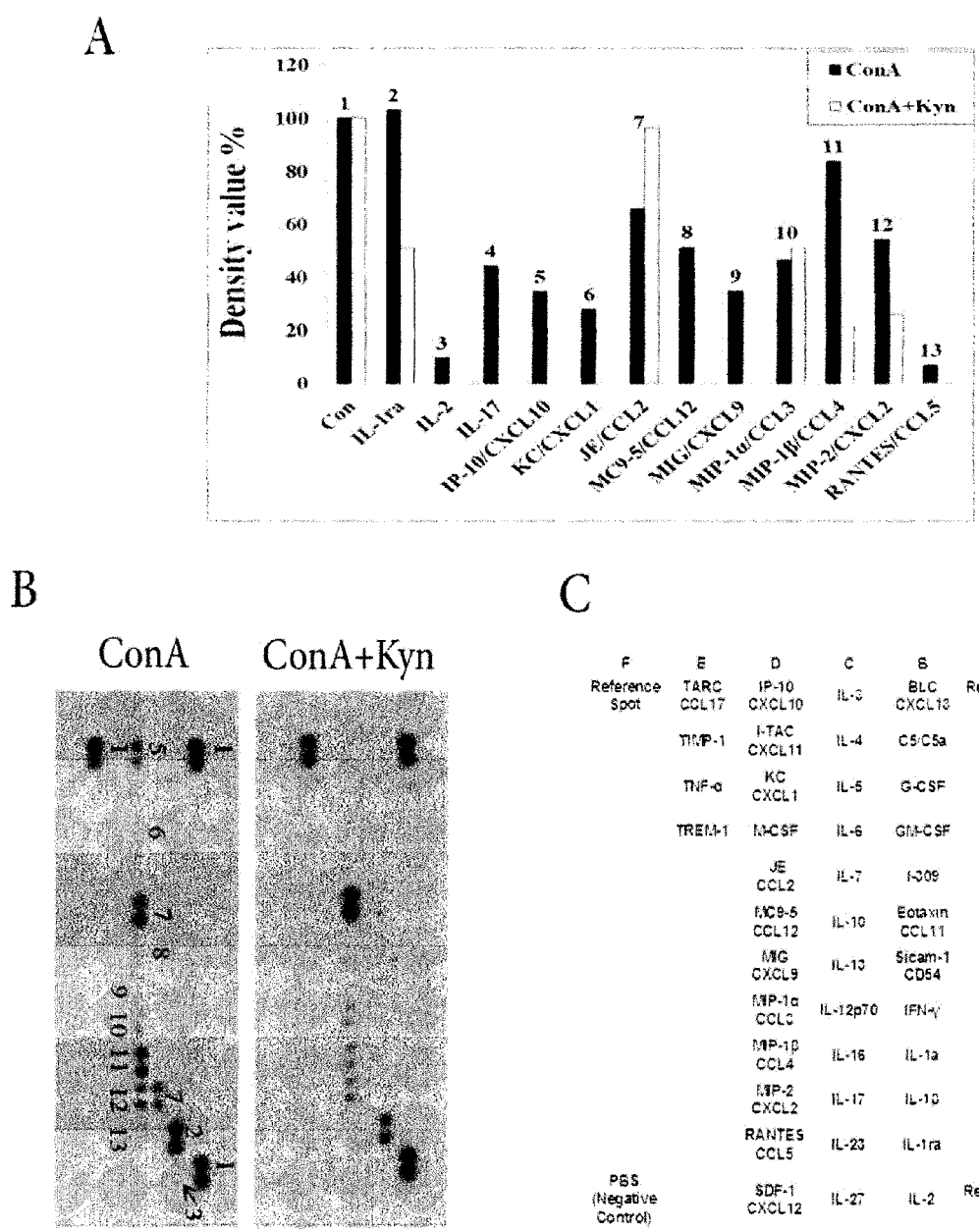
FIG. 18—Immune factor protein microarray in FS1 (DL-kynurenine) treated and untreated mouse splenocytes—shows that FS1 has immune suppressive effect on some proinflammatory cytokine and chemokine production, like IL-1, IL-2, CXCL9, and CXCL10 and FS1 shows a significant decrease in IL-17 production, which is thought to have an important role in inflammation. Panel A: shows activated splenocytes that were left untreated (ConA) or treated with 100 μg/mL of Kyn (ConA+Kyn) for 48 hrs, at which time the conditioned media (CM) was collected from untreated and treated cells and was then exposed to a Proteome Profiler Antibody Array™ membrane with density value percentages are shown for both the untreated and treated cells for each reference spot as shown in Pane B. Panel B: shows signals identified by Proteome Profiler Antibody Array membrane. Panel C: shows spot number shown in panel B represents reference protein.

Example 12—Kynurenine and Metabolites/Analogues have Significant Effects on Splenocytes The findings in FIG. 17 showed that, there was almost 5-fold reduction in conA-induced splenocyte proliferation following treatment with 100 and 150 µg/ml D-Kynurenine, L-Kynurenine or DL-Kynurenine after 96 hours (P<0.05), although splenocyte proliferation significantly reduced about 2-fold by D-Kynurenine, L-Kynurenine and DL-Kynurenine at 100 and 150 µg/ml after 48 hours. FS2 has less effect on proliferation than other metabolites. The findings in FIG. 18 showed that FS1 has immune suppressive effect on some of the proinflammatory cytokine and chemokine production, like IL-1, IL-2, CXCL9, and CXCL10. Besides it can significantly decrease IL-17 production which is thought to have an important role in inflammation.

Figure 19:
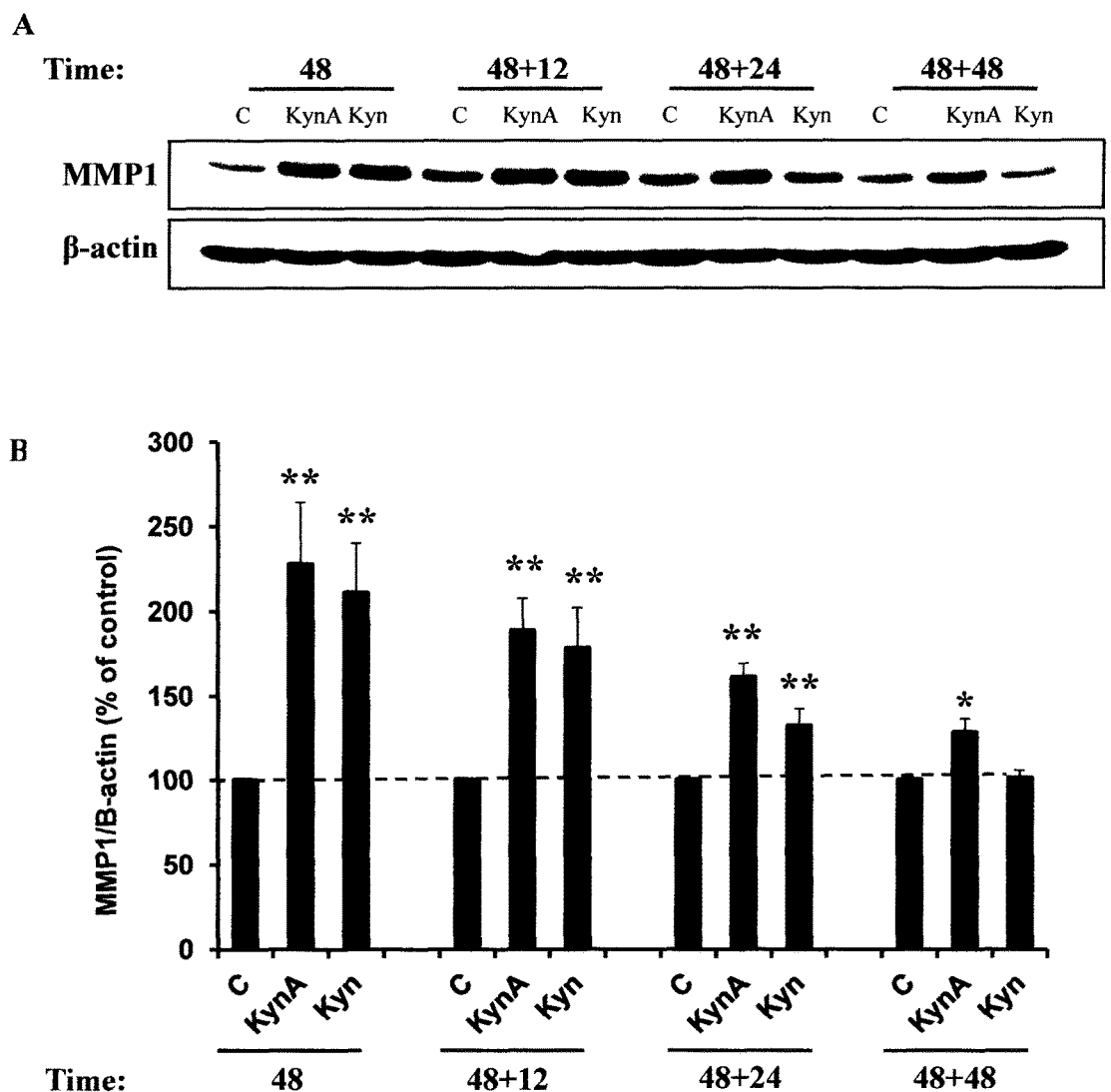
FIG. 19—Lasting effect of FS1 and FS2 on MMP1 expression in human dermal fibroblasts. Panel A: shows the lasting effect of kynurenine (FS1) and kynurenic acid (FS2) on MMP1 expression, where fibroblasts were treated with FS1 or FS2 (100 μg/ml) for 48 hours and the medium was replaced and cells were harvested immediately, and at 12, 24, and 48 hours after treatment removal, followed evaluation of MMP1 expression in dermal fibroblasts using Western blotting. Panel B: shows the MMP1/β-actin expression ratio as calculated in treated fibroblasts. Data is mean±SEM of 4 independent experiments (*P-value<0.05 and **P-value<0.01, n=4).

Example 13—Lasting Effect of Kynurenic Acid and Kynurenine on MMP1 Expression in Fibroblasts To determine the lasting effect of kynurenic acid (KynA) and kynurenine (Kyn) on MMP1 expression in fibroblasts, cells were treated with 100 μg/ml of the drug. Following 48 hours of treatment, the medium was changed with fresh medium and cells were then harvested at 0, 12, 24 or 48 hours post treatment removal. There was a marked increase in MMP1 expression in fibroblasts in response to either KynA or Kyn treatment at 48 hours after treatment. Following the removal of Kyn and KynA, the MMP1 expression remained significantly higher than the untreated cells for another 24 hours (FIG. 19A). Interestingly, while the MMP1 protein expression gradually reduced to normal levels within 48 hours after Kyn removal, the MMP1 expression in response to KynA remained higher than controls (FIG. 19A). FIG. 19B represents the quantitative analysis of data in FIG. 19A (*P-value<0.05, **P-value<0.01, n=4). From these results it appears that KynA has a longer lasting effect on expression of MMP-1 relative to Kyn in treated fibroblasts.

Although various embodiments are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to an embodiment of the present invention. The invention includes all embodiments and variations substantially as hereinbefore described and with reference to the examples and drawings.

REFERENCES

Gawronskao-Kozak B. et al. Wound Repair Regeneration (2006) Scarless skin repair in immunodeficient mice 14:265-276.
Ghahary A, Tredget E E, Chang L J, et al. (1998) Genetically modified dermal keratinocytes express high levels of transforming growth factor-β1. *J Invest Dermatol* 110: 800-805.
Kahari, V. M. and U. Saarialho-Kere (1997). "Matrix metalloproteinases in skin." *Exp Dermatol* 6(5): 199-213.
Kloeters O, Tandara A, Mustoe T (2007) Hypertrophic scar model in the rabbit ear: a reproducible model for studying scar tissue behavior with new observation on silicone gel sheeting for scar reduction. *Wound Repair Regen* 15:S40-S45.
Li Y, Tredget E E, Ghaffari A, et al. (2006) Local expression of indoleamine 2,3-dioxygenase protects engraftment of xenogeneic skin substitutes. *J Invest Dermatol* 126:128-136.
Li Y, Tredget E E, Kilani R T, et al. (2004) Expression of indoleamine 2,3-dioxygenase in dermal fibroblasts functions as a local immunosuppressive factor. *J Invest Dermatol* 122:953-964.
Rahmani-Neishaboor E, Yau F M, Jalili R, et al. (2010) Improvement of hypertrophic scarring by using topical anti-fibrogenic/anti-inflammatory factors in a rabbit ear model. *Wound Repair Regen* 18:401-408.
Salo, T., J. G. Lyons, et al. (1991). "Transforming growth factor-beta 1 up-regulates type IV collagenase expression in cultured human keratinocytes." *J Biol Chem* 266(18): 11436-41.
Saus, J., S. Quinones, et al. (1988). "The complete primary structure of human matrix metalloproteinase-3. Identity with stromelysin." J Biol Chem 263(14): 6742-5.
Scott, P. G., A. Ghahary, et al. (1994). *In: Advances in Structural Biology* 3: 157-201.
Tokikawa O, Kuroiwa T, Yamazaki F, et al. (1988) Mechanism of interferon-γ action: characterization of indoleamine 2,3-dioxygenase in cultured human cells by intefron-γ and evaluation of the enzyme-mediated tryptophan degradation in its anticellular activity. *J Biol Chem* 263:2041-2048.
Xie J L, Bian H N, Qi S H, et al. (2008) Basic fibroblast growth factor (bFGF) alleviates the scar of the rabbit ear model in wound healing. *Wound Repair Regen* 16:576-581.

What is claimed is:

1. A method of treating fibrotic disease, the method comprising administering to a subject in need thereof, a compound or pharmaceutically acceptable salt thereof, the compound having the structure of Formula I:

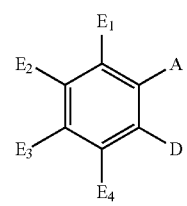

wherein,
$E_1$ is H, OH, $NH_2$, R, OR, SH, F, Cl, Br, or I;
$E_2$ is H, OH, $NH_2$, R, OR, SH, F, Cl, Br, or I;
$E_3$ is H, OH, $NH_2$, R, OR, SH, F, Cl, Br, or I;
$E_4$ is H, OH, $NH_2$, R, OR, SH, F, Cl, Br, or I;
R is a 1 to 6 carbon group that is optionally saturated, unsaturated, linear, branched linear, or cyclic;
A is H, or $NH_2$;
D is

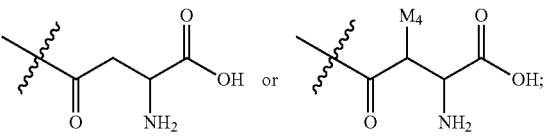

or
A and D form a 6 membered ring selected from the following:

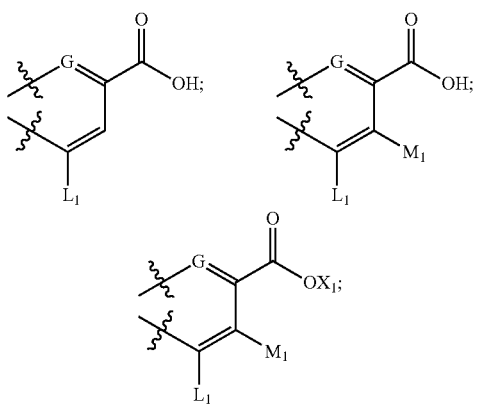

G is CH or N;
L₁ is OH, NH₂, or SH;
M₁ is H, OH, NH₂, SH, F, Cl, Br, or I;
M₄ is OH, NH₂, SH, F, Cl, Br, or I;
X₁ is H, OH, NH₂, SH, F, Cl, Br, or I;
wherein the fibrotic disease is selected from keloid; hypertrophic scaring; pulmonary fibrosis; kidney fibrosis; liver cirrhosis; endomyocardial fibrosis; mediastinal fibrosis; myelofibrosis; retroperitoneal fibrosis; progressive massive fibrosis; nephrogenic systemic fibrosis; old myocardial infarction; scleroderma; systemic sclerosis; and uterine fibroids.

2. The method of treating fibrotic disease of claim 1, wherein the subject is a mammal.

3. The method of claim 1, wherein
E₁ is H, OH, NH₂, OCH₃, CH₃, SH, F, Cl, Br, or I;
E₂ is H, OH, NH₂, OCH₃, CH₃, SH, F, Cl, Br, or I;
E₃ is H, OH, NH₂, OCH₃, CH₃, SH, F, Cl, Br, or I;
E₄ is H, OH, NH₂, OCH₃, CH₃, SH, F, Cl, Br, or I;
A is H or NH₂;
D is

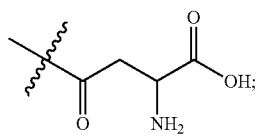 [SMILES: *C(=O)CC(N)C(=O)O]

or
A and D form a 6 membered ring selected from the following:

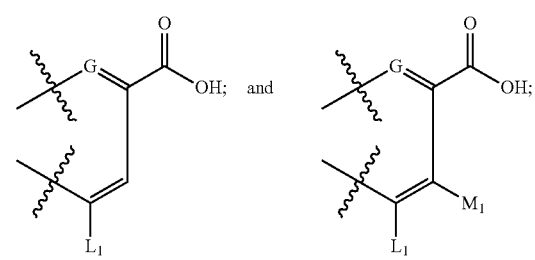

G is CH or N;
L₁ is OH, NH₂, or SH;
M₁ is H, OH, NH₂, SH, F, Cl, Br, or I; and
M4 is OH, NH₂, SH, F, Cl, Br, or I.

4. The method of claim 1, wherein
E₁ is H, OH, NH₂, OCH₃, or CH₃;
E₂ is H, OH, NH₂, OCH₃, or CH₃;
E₃ is H, OH, NH₂, OCH₃, or CH₃;
E₄ is H, OH, NH₂, OCH₃, or CH₃;
A is H or NH₂;
D is

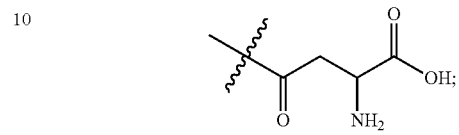

or
A and D form a 6 membered ring selected from the following:

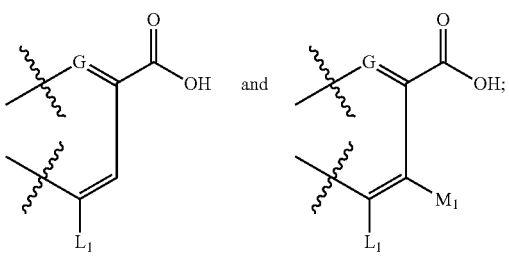

G is CH or N;
L₁ is OH or NH₂; and
M₁ is H, OH, or NH₂.

5. The method of claim 1, wherein
E₁ is H, OH, NH₂, OCH₃, or CH₃;
E₂ is H, OH, NH₂, OCH₃, or CH₃;
E₃ is H, OH, NH₂, OCH₃, or CH₃;
E₄ is H, OH, NH₂, OCH₃, or CH₃;
A is H, or NH₂; and
D is

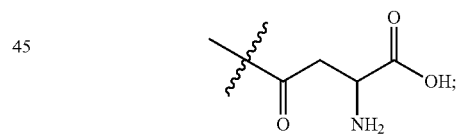

A and D form a 6 membered ring having the following structure:

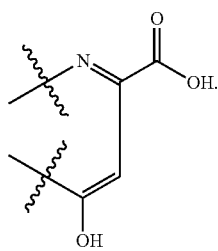 [SMILES: */N=C(\C=C(/*)O)C(=O)O]

6. The method of claim 1, wherein
E₁ is H, OH, or NH₂;
E₂ is H, OH, or NH₂;

$E_3$ is H, OH, or $NH_2$;
$E_4$ is H, OH, or $NH_2$;
A is H, or $NH_2$; and
D is

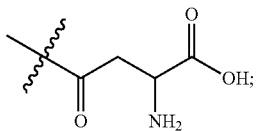 [SMILES: *C(=O)CC(N)C(=O)O]

or

A and D form a 6 membered ring having the following structure:

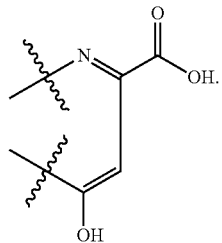 [SMILES: */N=C(\C=C(/*)O)C(=O)O]

7. The method of claim 1, wherein the compound has the structure of Formula II:

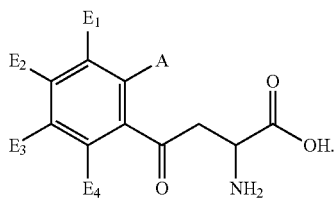

II

8. The method of claim 1, wherein the compound has the structure of Formula III:

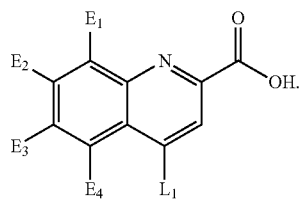

III

9. The method of claim 8, wherein $L_1$ is OH or $NH_2$.
10. The method of claim 8, wherein $L_1$ is OH.
11. The method of claim 1, wherein
$E_1$ is H or OH;
$E_2$ is H, OH, or $NH_2$;
$E_3$ is H, OH, or $NH_2$; and
$E_4$ is H, OH, or $NH_2$.
12. The method of claim 1, wherein
$E_1$ is H, OH, or $NH_2$;
$E_2$ is H or OH;
$E_3$ is H, OH, or $NH_2$; and
$E_4$ is H, OH, or $NH_2$.
13. The method of claim 1, wherein
$E_1$ is H, OH, or $NH_2$;
$E_2$ is H, OH, or $NH_2$;
$E_3$ is H or OH; and
$E_4$ is H, OH, or $NH_2$.
14. The method of claim 1, wherein
$E_1$ is H, OH, or $NH_2$;
$E_2$ is H, OH, or $NH_2$;
$E_3$ is H or OH; and
$E_4$ is H or $NH_2$.
15. The method of claim 1, wherein
$E_1$ is H or OH;
$E_2$ is H or OH;
$E_3$ is H or OH; and
$E_4$ is H or $NH_2$.
16. The method of claim 1, wherein the compound is selected from the following:

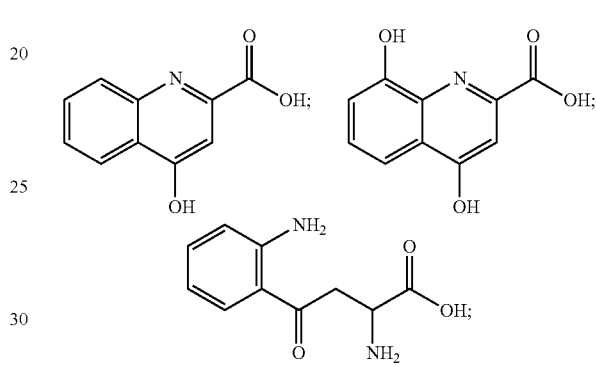

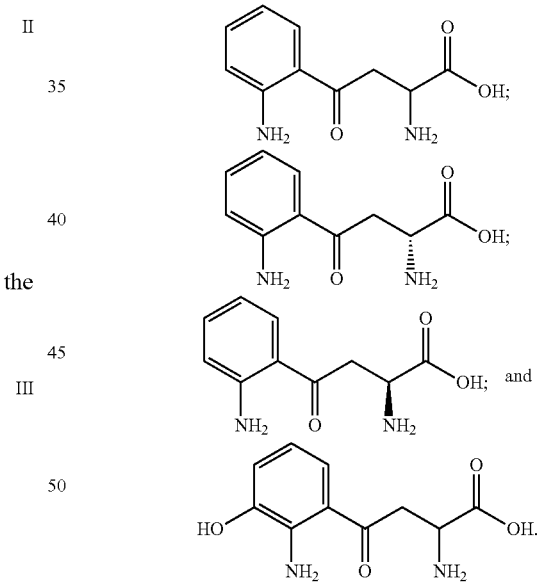

17. The method of claim 1, wherein the compound is selected from the following:

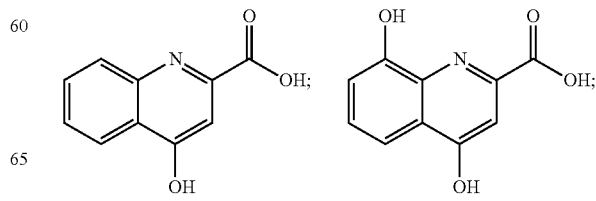

-continued
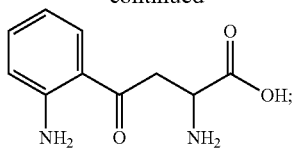
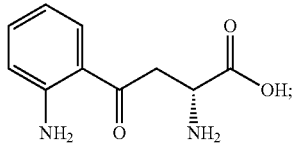
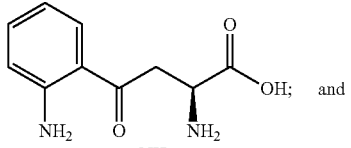
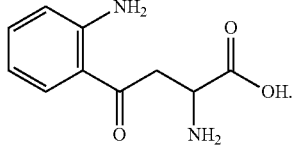
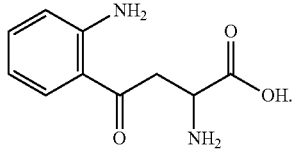
* * * * *

UNITED STATES PATENT AND TRADEMARK OFFICE
CERTIFICATE OF CORRECTION

PATENT NO.       : 9,737,523 B2
APPLICATION NO.  : 14/896269
DATED            : August 22, 2017
INVENTOR(S)      : Aziz Ghahary et al.

It is certified that error appears in the above-identified patent and that said Letters Patent is hereby corrected as shown below:

In the Specification

Column 3,
Line 34, "may be CH or N;" should read -- G may be CH or N; --.

Column 11,
Line 20, "of MMP-1 to 3-actin" should read -- of MMP-1 to β-actin --.

Column 12,
Line 47, "MT cell" should read -- MTT cell --.

Column 20,
Lines 64-65, "(Figure A, right panel)." should read -- (Figure 1A, right panel). --.

Figure 10:
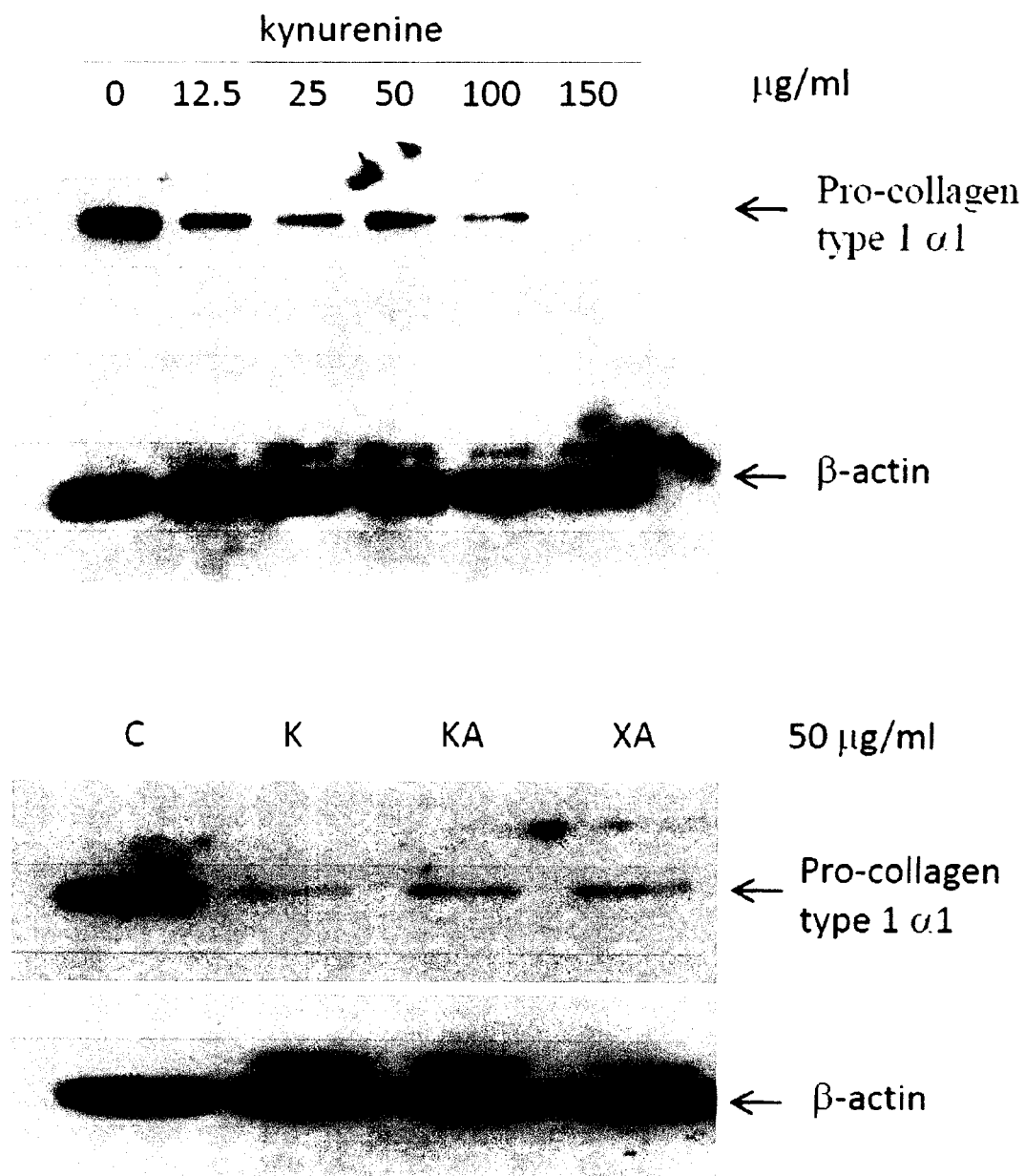
FIG. 10—Effect of kynurenine, kynurenic acid, and xanthurenic acid on procollagen type 1 expression in dermal fibroblasts—shows human dermal fibroblasts were treated with indicated concentrations of kynurenine for 48 hours (top), where cells were harvested and lysed with cell lysis buffer and a total 50 μg of protein was fractionated by 8% SDS-PAGE, before Western blotting was performed by using antibody against pro-collagen. β-actin was used a loading control, with kynurenic acid (KA) and xanthurenic acid (XA) also tested (bottom).

Column 23,
Lines 15-16, "cells with to M and 30 μM" should read -- cells with 10 μM and 30 μM --.
Line 29, "As shown in Figure to" should read -- As shown in Figure 10 --.
Line 37, "(Figure to" should read -- (Figure 10 --.

Signed and Sealed this
Twentieth Day of March, 2018

Andrei Iancu
*Director of the United States Patent and Trademark Office*

UNITED STATES PATENT AND TRADEMARK OFFICE
CERTIFICATE OF CORRECTION

PATENT NO. : 9,737,523 B2  
APPLICATION NO. : 14/896269  
DATED : August 22, 2017  
INVENTOR(S) : Aziz Ghahary et al.

Page 1 of 1

It is certified that error appears in the above-identified patent and that said Letters Patent is hereby corrected as shown below:

In the Claims

Column 27:  
Line 25, "hypertrophic scaring;" should read --hypertrophic scarring;--.

Signed and Sealed this  
Thirtieth Day of August, 2022

Katherine Kelly Vidal  
*Director of the United States Patent and Trademark Office*